US012714369B2

(12) United States Patent
Kiani et al.

(10) Patent No.: US 12,714,369 B2
(45) Date of Patent: Aug. 25, 2026

(54) OPTICAL SENSOR TAPE

(71) Applicant: Masimo Corporation, Irvine, CA (US)

(72) Inventors: Massi Joe E. Kiani, Laguna Niguel, CA (US); Ammar Al-Ali, San Juan Capistrano, CA (US); Benjamin C. Triman, Rancho Santa Margarita, CA (US); Chad A DeJong, Los Angeles, CA (US)

(73) Assignee: Masimo Corporation, Irvine, CA (US)

(*) Notice: Subject to any disclaimer, the term of this patent is extended or adjusted under 35 U.S.C. 154(b) by 62 days.

(21) Appl. No.: 18/650,832

(22) Filed: Apr. 30, 2024

(65) Prior Publication Data

US 2024/0277292 A1 Aug. 22, 2024

Related U.S. Application Data

(63) Continuation of application No. 17/518,427, filed on Nov. 3, 2021, now Pat. No. 12,004,877, which is a continuation of application No. 15/582,082, filed on Apr. 28, 2017, now Pat. No. 11,191,484.

(60) Provisional application No. 62/329,451, filed on Apr. 29, 2016.

(51) Int. Cl.
*A61B 5/00* (2006.01)
*A61B 5/1455* (2006.01)

(52) U.S. Cl.
CPC ........ *A61B 5/6833* (2013.01); *A61B 5/14551* (2013.01)

(58) Field of Classification Search
CPC .... A61B 5/6833; A61B 5/14551; A61B 5/145
See application file for complete search history.

(56) References Cited

U.S. PATENT DOCUMENTS

| | | | |
|---|---|---|---|
| 3,547,120 | A | 12/1970 | Grossman |
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Hink et al. |
| 5,163,438 | A | 11/1992 | Gordon et al. |
| 5,170,786 | A | 12/1992 | Thomas et al. |
| 5,319,355 | A | 6/1994 | Russek |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |

(Continued)

OTHER PUBLICATIONS

US 2024/0016391 A1, 01/2024, Lapotko et al. (withdrawn)

*Primary Examiner* — Abid A Mustansir
(74) *Attorney, Agent, or Firm* — Knobbe, Martens Olson & Bear, LLP

(57) ABSTRACT

Various sensor tapes can improve securing of a non-invasive optical sensor to a surface of a medium for taking noninvasive measurement of characteristics of the medium. The sensor tape can taper from a wide end to a narrow end. The sensor tape can transition from a wide portion to a narrow portion in a step-like change or slope. The sensor tape can have staggered portions. The various tapes can be used with an L-shaped sensor. The various tapes can increase contact surface between the surface of the medium and an adhesive side of the tape so as to reduce motion-induced noise.

16 Claims, 27 Drawing Sheets

(56) References Cited

U.S. PATENT DOCUMENTS 5,452,717 A 9/1995 Branigan et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,685,299 A 11/1997 Diab et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,987,343 A 11/1999 Kinast
5,995,855 A 11/1999 Kiani et al.
5,997,343 A 12/1999 Mills et al.
5,999,834 A * 12/1999 Wang .................. A61B 5/6833 600/344
6,002,952 A 12/1999 Diab et al.
6,010,937 A 1/2000 Karam et al.
6,011,986 A 1/2000 Diab et al.
6,027,452 A 2/2000 Flaherty et al.
6,036,642 A 3/2000 Diab et al.
6,040,578 A 3/2000 Malin et al.
6,045,509 A 4/2000 Caro et al.
6,066,204 A 5/2000 Haven
6,067,462 A 5/2000 Diab et al.
6,081,735 A 6/2000 Diab et al.
6,088,607 A 7/2000 Diab et al.
6,110,522 A 8/2000 Lepper, Jr. et al.
6,112,107 A 8/2000 Hannula
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,255,708 B1 7/2001 Sudharsanan et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,280,381 B1 8/2001 Malin et al.
6,285,896 B1 9/2001 Tobler et al.
6,301,493 B1 10/2001 Marro et al.
6,308,089 B1 10/2001 von der Ruhr et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,466,809 B1 * 10/2002 Riley .................. A61B 5/6838 600/344
6,470,199 B1 10/2002 Kopotic et al.
6,487,429 B2 11/2002 Hockersmith et al.
6,501,975 B2 12/2002 Diab et al.
6,505,059 B1 1/2003 Kollias et al.
6,515,273 B2 2/2003 Al-Ali
6,519,487 B1 2/2003 Parker
6,525,386 B1 2/2003 Mills et al.
6,526,300 B1 2/2003 Kiani et al.
6,534,012 B1 3/2003 Hazen et al.
6,541,756 B2 4/2003 Schulz et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,643,530 B2 11/2003 Diab et al.
6,650,917 B2 11/2003 Diab et al.
6,654,624 B2 11/2003 Diab et al.
6,658,276 B2 12/2003 Kiani et al.
6,661,161 B1 12/2003 Lanzo et al.
6,671,531 B2 12/2003 Al-Ali
6,678,543 B2 1/2004 Diab et al.
6,684,090 B2 1/2004 Ali et al.
6,684,091 B2 1/2004 Parker
6,697,656 B1 2/2004 Al-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,721,582 B2 4/2004 Trepagnier et al.
6,721,585 B1 4/2004 Parker
6,725,075 B2 4/2004 Al-Ali
6,728,560 B2 4/2004 Kollias et al.
6,735,459 B2 5/2004 Parker
6,738,652 B2 5/2004 Mattu et al.
6,745,060 B2 6/2004 Diab et al.
6,760,607 B2 7/2004 Al-Ali
6,770,028 B1 8/2004 Ali et al.
6,771,994 B2 8/2004 Kiani et al.
6,788,965 B2 9/2004 Ruchti et al.
6,792,300 B1 9/2004 Diab et al.
6,813,511 B2 11/2004 Diab et al.
6,816,241 B2 11/2004 Grubisic
6,816,741 B2 11/2004 Diab
6,822,564 B2 11/2004 Ai-Ali

(56) References Cited

U.S. PATENT DOCUMENTS 6,826,419 B2 11/2004 Diab et al.
6,830,711 B2 12/2004 Mills et al.
6,850,787 B2 2/2005 Weber et al.
6,850,788 B2 2/2005 Al-Ali
6,852,083 B2 2/2005 Caro et al.
6,861,639 B2 3/2005 Al-Ali
6,876,931 B2 4/2005 Lorenz et al.
6,898,452 B2 5/2005 Al-Ali et al.
6,920,345 B2 7/2005 Al-Ali et al.
6,931,268 B1 8/2005 Kiani-Azarbayjany et al.
6,934,570 B2 8/2005 Kiani et al.
6,939,305 B2 9/2005 Flaherty et al.
6,943,348 B1 9/2005 Coffin IV
6,950,687 B2 9/2005 Al-Ali
6,956,649 B2 10/2005 Acosta et al.
6,961,598 B2 11/2005 Diab
6,970,792 B1 11/2005 Diab
6,979,812 B2 12/2005 Al-Ali
6,985,764 B2 1/2006 Mason et al.
6,990,364 B2 1/2006 Ruchti et al.
6,993,371 B2 1/2006 Kiani et al.
6,996,427 B2 2/2006 Ali et al.
6,998,247 B2 2/2006 Monfre et al.
6,999,904 B2 2/2006 Weber et al.
7,003,338 B2 2/2006 Weber et al.
7,003,339 B2 2/2006 Diab et al.
7,015,451 B2 3/2006 Dalke et al.
7,024,233 B2 4/2006 Ali et al.
7,027,849 B2 4/2006 Al-Ali
7,030,749 B2 4/2006 Al-Ali
7,039,449 B2 5/2006 Al-Ali
7,041,060 B2 5/2006 Flaherty et al.
7,044,918 B2 5/2006 Diab
7,048,687 B1 5/2006 Reuss et al.
7,067,893 B2 6/2006 Mills et al.
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,132,641 B2 11/2006 Schulz et al.
7,133,710 B2 11/2006 Acosta et al.
7,142,901 B2 11/2006 Kiani et al.
7,149,561 B2 12/2006 Diab
7,186,966 B2 3/2007 Al-Ali
7,190,261 B2 3/2007 Ai-Ali
7,215,984 B2 5/2007 Diab et al.
7,215,986 B2 5/2007 Diab et al.
7,221,971 B2 5/2007 Diab et al.
7,225,006 B2 5/2007 Al-Ali et al.
7,225,007 B2 5/2007 Al-Ali et al.
RE39,672 E 6/2007 Shehada et al.
7,239,905 B2 7/2007 Kiani-Azarbayjany et al.
7,245,953 B1 7/2007 Parker
7,254,429 B2 8/2007 Schurman et al.
7,254,431 B2 8/2007 Al-Ali et al.
7,254,433 B2 8/2007 Diab et al.
7,254,434 B2 8/2007 Schulz et al.
7,272,425 B2 9/2007 Al-Ali
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,395,158 B2 7/2008 Monfre et al.
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,471,969 B2 12/2008 Diab et al.
7,471,971 B2 12/2008 Diab et al.
7,483,729 B2 1/2009 Al-Ali et al.
7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Ai-Ali
7,510,849 B2 3/2009 Schurman et al.
7,514,725 B2 4/2009 Wojtczuk et al.
7,519,406 B2 4/2009 Blank et al.
7,526,328 B2 4/2009 Diab et al.
D592,507 S 5/2009 Wachman et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,593,230 B2 9/2009 Abul-Haj et al.
7,596,398 B2 9/2009 Al-Ali et al.
7,606,608 B2 10/2009 Blank et al.
7,618,375 B2 11/2009 Flaherty et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,791,155 B2 9/2010 Diab
7,801,581 B2 9/2010 Diab
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,865,222 B2 1/2011 Weber et al.
7,873,497 B2 1/2011 Weber et al.
7,880,606 B2 2/2011 Al-Ali
7,880,626 B2 2/2011 Al-Ali et al.
7,891,355 B2 2/2011 Al-Ali et al.
7,894,868 B2 2/2011 Al-Ali et al.
7,899,507 B2 3/2011 Al-Ali et al.
7,904,132 B2 3/2011 Weber et al.
7,909,772 B2 3/2011 Popov et al.
7,910,875 B2 3/2011 Al-Ali
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,951,086 B2 5/2011 Flaherty et al.
7,957,780 B2 6/2011 Lamego et al.

(56) References Cited

U.S. PATENT DOCUMENTS 7,962,188 B2 6/2011 Kiani et al.
7,962,190 B1 6/2011 Diab et al.
7,976,472 B2 7/2011 Kiani
7,988,637 B2 8/2011 Diab
7,990,382 B2 8/2011 Kiani
7,991,446 B2 8/2011 Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,727 B2 10/2011 Schurman et al.
8,036,728 B2 10/2011 Diab et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,203,438 B2 6/2012 Kiani et al.
8,203,704 B2 6/2012 Merritt et al.
8,204,566 B2 6/2012 Schurman et al.
8,219,172 B2 7/2012 Schurman et al.
8,224,411 B2 7/2012 Al-Ali et al.
8,228,181 B2 7/2012 Al-Ali
8,229,532 B2 7/2012 Davis
8,229,533 B2 7/2012 Diab et al.
8,233,955 B2 7/2012 Al-Ali et al.
8,244,325 B2 8/2012 Al-Ali et al.
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,274,360 B2 9/2012 Sampath et al.
8,280,473 B2 10/2012 Al-Ali
8,301,217 B2 10/2012 Al-Ali et al.
8,306,596 B2 11/2012 Schurman et al.
8,310,336 B2 11/2012 Muhsin et al.
8,315,683 B2 11/2012 Al-Ali et al.
RE43,860 E 12/2012 Parker
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,364,223 B2 1/2013 Al-Ali et al.
8,364,226 B2 1/2013 Diab et al.
8,374,665 B2 2/2013 Lamego
8,385,995 B2 2/2013 Al-Ali et al.
8,385,996 B2 2/2013 Smith et al.
8,388,353 B2 3/2013 Kiani et al.
8,399,822 B2 3/2013 Al-Ali
8,401,602 B2 3/2013 Kiani
8,405,608 B2 3/2013 Al-Ali et al.
8,414,499 B2 4/2013 Al-Ali et al.
8,418,524 B2 4/2013 Al-Ali
8,423,106 B2 4/2013 Lamego et al.
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellott et al.
8,471,713 B2 6/2013 Poeze et al.
8,473,020 B2 6/2013 Kiani et al.
8,483,787 B2 7/2013 Al-Ali et al.
8,489,364 B2 7/2013 Weber et al.
8,498,684 B2 7/2013 Weber et al.
8,504,128 B2 8/2013 Blank et al.
8,509,867 B2 8/2013 Workman et al.
8,515,509 B2 8/2013 Bruinsma et al.
8,523,781 B2 9/2013 Al-Ali
8,529,301 B2 9/2013 Al-Ali et al.
8,532,727 B2 9/2013 Ali et al.
8,532,728 B2 9/2013 Diab et al.
D692,145 S 10/2013 Al-Ali et al.
8,547,209 B2 10/2013 Kiani et al.
8,548,548 B2 10/2013 Al-Ali
8,548,549 B2 10/2013 Schurman et al.
8,548,550 B2 10/2013 Al-Ali et al.
8,560,032 B2 10/2013 Al-Ali et al.
8,560,034 B1 10/2013 Diab et al.
8,570,167 B2 10/2013 Al-Ali
8,570,503 B2 10/2013 Vo et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,581,732 B2 11/2013 Al-Ali et al.
8,584,345 B2 11/2013 Al-Ali et al.
8,588,880 B2 11/2013 Abdul-Hafiz et al.
8,600,467 B2 12/2013 Al-Ali et al.
8,606,342 B2 12/2013 Diab
8,626,255 B2 1/2014 Al-Ali et al.
8,630,691 B2 1/2014 Lamego et al.
8,634,889 B2 1/2014 Al-Ali et al.
8,641,631 B2 2/2014 Sierra et al.
8,652,060 B2 2/2014 Al-Ali
8,663,107 B2 3/2014 Kiani
8,666,468 B1 3/2014 Al-Ali
8,667,967 B2 3/2014 Al-Ali et al.
8,670,811 B2 3/2014 O'Reilly
8,670,814 B2 3/2014 Diab et al.
8,676,286 B2 3/2014 Weber et al.
8,682,407 B2 3/2014 Al-Ali
RE44,823 E 4/2014 Parker
RE44,875 E 4/2014 Kiani et al.
8,688,183 B2 4/2014 Bruinsma et al.
8,690,799 B2 4/2014 Telfort et al.
8,700,112 B2 4/2014 Kiani
8,702,627 B2 4/2014 Telfort et al.
8,706,179 B2 4/2014 Parker
8,712,494 B1 4/2014 MacNeish, III et al.
8,715,206 B2 5/2014 Telfort et al.
8,718,735 B2 5/2014 Lamego et al.
8,718,737 B2 5/2014 Diab et al.
8,718,738 B2 5/2014 Blank et al.
8,720,249 B2 5/2014 Al-Ali
8,721,541 B2 5/2014 Al-Ali et al.
8,721,542 B2 5/2014 Al-Ali et al.
8,723,677 B1 5/2014 Kiani
8,740,792 B1 6/2014 Kiani et al.
8,754,776 B2 6/2014 Poeze et al.
8,755,535 B2 6/2014 Telfort et al.
8,755,856 B2 6/2014 Diab et al.
8,755,872 B1 6/2014 Marinow
8,761,850 B2 6/2014 Lamego
8,764,671 B2 7/2014 Kiani
8,768,423 B2 7/2014 Shakespeare et al.
8,771,204 B2 7/2014 Telfort et al.
8,777,634 B2 7/2014 Kiani et al.
8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Al-Ali
8,801,613 B2 8/2014 Al-Ali et al.
8,821,397 B2 9/2014 Al-Ali et al.

(56) References Cited

U.S. PATENT DOCUMENTS 8,821,415 B2 9/2014 Al-Ali et al.
8,830,449 B1 9/2014 Lamego et al.
8,831,700 B2 9/2014 Schurman et al.
8,840,549 B2 9/2014 Al-Ali et al.
8,847,740 B2 9/2014 Kiani et al.
8,849,365 B2 9/2014 Smith et al.
8,852,094 B2 10/2014 Al-Ali et al.
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,909,310 B2 12/2014 Lamego et al.
8,911,377 B2 12/2014 Al-Ali
8,912,909 B2 12/2014 Al-Ali et al.
8,920,317 B2 12/2014 Al-Ali et al.
8,921,699 B2 12/2014 Al-Ali et al.
8,922,382 B2 12/2014 Al-Ali et al.
8,929,964 B2 1/2015 Al-Ali et al.
8,942,777 B2 1/2015 Diab et al.
8,948,834 B2 2/2015 Diab et al.
8,948,835 B2 2/2015 Diab
8,965,471 B2 2/2015 Lamego
8,983,564 B2 3/2015 Al-Ali
8,989,831 B2 3/2015 Al-Ali et al.
8,996,085 B2 3/2015 Kiani et al.
8,998,809 B2 4/2015 Kiani
9,028,429 B2 5/2015 Telfort et al.
9,037,207 B2 5/2015 Al-Ali et al.
9,060,721 B2 6/2015 Reichgott et al.
9,066,666 B2 6/2015 Kiani
9,066,680 B1 6/2015 Al-Ali et al.
9,072,474 B2 7/2015 Al-Ali et al.
9,078,560 B2 7/2015 Schurman et al.
9,084,569 B2 7/2015 Weber et al.
9,095,316 B2 8/2015 Welch et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Ai-Ali
9,119,595 B2 9/2015 Lamego
9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
9,153,112 B1 10/2015 Kiani et al.
9,153,121 B2 10/2015 Kiani et al.
9,161,696 B2 10/2015 Al-Ali et al.
9,161,713 B2 10/2015 Al-Ali et al.
9,167,995 B2 10/2015 Lamego et al.
9,176,141 B2 11/2015 Al-Ali et al.
9,186,102 B2 11/2015 Bruinsma et al.
9,192,312 B2 11/2015 Al-Ali
9,192,329 B2 11/2015 Al-Ali
9,192,351 B1 11/2015 Telfort et al.
9,195,385 B2 11/2015 Al-Ali et al.
9,211,072 B2 12/2015 Kiani
9,211,095 B1 12/2015 Al-Ali
9,218,454 B2 12/2015 Kiani et al.
9,226,696 B2 1/2016 Kiani
9,241,662 B2 1/2016 Al-Ali et al.
9,245,668 B1 1/2016 Vo et al.
9,259,185 B2 2/2016 Abdul-Hafiz et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,928 B1 4/2016 Al-Ali et al.
9,323,894 B2 4/2016 Kiani
D755,392 S 5/2016 Hwang et al.
9,326,712 B1 5/2016 Kiani
9,333,316 B2 5/2016 Kiani
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-Ali et al.
9,375,185 B2 6/2016 Ali et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
9,408,542 B1 8/2016 Kinast et al.
9,436,645 B2 9/2016 Al-Ali et al.
9,445,759 B1 9/2016 Lamego et al.
9,466,919 B2 10/2016 Kiani et al.
9,474,474 B2 10/2016 Lamego et al.
9,480,422 B2 11/2016 Al-Ali
9,480,435 B2 11/2016 Olsen
9,492,110 B2 11/2016 Al-Ali et al.
9,510,779 B2 12/2016 Poeze et al.
9,517,024 B2 12/2016 Kiani et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
9,591,975 B2 3/2017 Dalvi et al.
9,622,692 B2 4/2017 Lamego et al.
9,622,693 B2 4/2017 Diab
D788,312 S 5/2017 Al-Ali et al.
9,636,055 B2 5/2017 Al Ali et al.
9,636,056 B2 5/2017 Al-Ali
9,649,054 B2 5/2017 Lamego et al.
9,662,052 B2 5/2017 Al-Ali et al.
9,668,679 B2 6/2017 Schurman et al.
9,668,680 B2 6/2017 Bruinsma et al.
9,668,703 B2 6/2017 Al-Ali
9,675,286 B2 6/2017 Diab
9,687,160 B2 6/2017 Kiani
9,693,719 B2 7/2017 Al-Ali et al.
9,693,737 B2 7/2017 Al-Ali
9,697,928 B2 7/2017 Al-Ali et al.
9,717,425 B2 8/2017 Kiani et al.
9,717,458 B2 8/2017 Lamego et al.
9,724,016 B1 8/2017 Al-Ali et al.
9,724,024 B2 8/2017 Ai-Ali
9,724,025 B1 8/2017 Kiani et al.
9,730,640 B2 8/2017 Diab et al.
9,743,887 B2 8/2017 Al-Ali et al.
9,749,232 B2 8/2017 Sampath et al.
9,750,442 B2 9/2017 Olsen
9,750,443 B2 9/2017 Smith et al.
9,750,461 B1 9/2017 Telfort
9,775,545 B2 10/2017 Al-Ali et al.
9,775,546 B2 10/2017 Diab et al.
9,775,570 B2 10/2017 Al-Ali
9,778,079 B1 10/2017 Al-Ali et al.
9,782,077 B2 10/2017 Lamego et al.
9,782,110 B2 10/2017 Kiani
9,787,568 B2 10/2017 Lamego et al.
9,788,735 B2 10/2017 Al-Ali
9,788,768 B2 10/2017 Al-Ali et al.
9,795,300 B2 10/2017 Al-Ali
9,795,310 B2 10/2017 Al-Ali
9,795,358 B2 10/2017 Telfort et al.
9,795,739 B2 10/2017 Al-Ali et al.

(56) References Cited

U.S. PATENT DOCUMENTS

| | | | |
|---|---|---|---|
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| 9,833,152 | B2 | 12/2017 | Kiani et al. |
| 9,833,180 | B2 | 12/2017 | Shakespeare et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Ai-Ali |
| 9,848,807 | B2 | 12/2017 | Lamego |
| 9,861,298 | B2 | 1/2018 | Eckerbom et al. |
| 9,861,304 | B2 | 1/2018 | Al-Ali et al. |
| 9,861,305 | B1 | 1/2018 | Weber et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| 9,891,079 | B2 | 2/2018 | Dalvi |
| 9,895,107 | B2 | 2/2018 | Al-Ali et al. |
| 9,913,617 | B2 | 3/2018 | Al-Ali et al. |
| 9,924,893 | B2 | 3/2018 | Schurman et al. |
| 9,924,897 | B1 | 3/2018 | Abdul-Hafiz |
| 9,936,917 | B2 | 4/2018 | Poeze et al. |
| 9,943,269 | B2 | 4/2018 | Muhsin et al. |
| 9,949,676 | B2 | 4/2018 | Al-Ali |
| 9,955,937 | B2 | 5/2018 | Telfort |
| 9,965,946 | B2 | 5/2018 | Al-Ali et al. |
| 9,980,667 | B2 | 5/2018 | Kiani et al. |
| D820,865 | S | 6/2018 | Muhsin et al. |
| 9,986,919 | B2 | 6/2018 | Lamego et al. |
| 9,986,952 | B2 | 6/2018 | Dalvi et al. |
| 9,989,560 | B2 | 6/2018 | Poeze et al. |
| 9,993,207 | B2 | 6/2018 | Al-Ali et al. |
| 10,007,758 | B2 | 6/2018 | Al-Ali et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,032,002 | B2 | 7/2018 | Kiani et al. |
| 10,039,482 | B2 | 8/2018 | Al-Ali et al. |
| 10,052,037 | B2 | 8/2018 | Kinast et al. |
| 10,058,275 | B2 | 8/2018 | Al-Ali et al. |
| 10,064,562 | B2 | 9/2018 | Al-Ali |
| 10,086,138 | B1 | 10/2018 | Novak, Jr. |
| 10,092,200 | B2 | 10/2018 | Al-Ali et al. |
| 10,092,249 | B2 | 10/2018 | Kiani et al. |
| 10,098,550 | B2 | 10/2018 | Al-Ali et al. |
| 10,098,591 | B2 | 10/2018 | Al-Ali et al. |
| 10,098,610 | B2 | 10/2018 | Al-Ali et al. |
| 10,111,591 | B2 | 10/2018 | Dyell et al. |
| D833,624 | S | 11/2018 | DeJong et al. |
| 10,123,726 | B2 | 11/2018 | Al-Ali et al. |
| 10,123,729 | B2 | 11/2018 | Dyell et al. |
| 10,130,289 | B2 | 11/2018 | Al-Ali et al. |
| 10,130,291 | B2 | 11/2018 | Schurman et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,296 | B2 | 1/2019 | Al-Ali et al. |
| 10,188,331 | B1 | 1/2019 | Kiani et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,194,847 | B2 | 2/2019 | Al-Ali |
| 10,194,848 | B1 | 2/2019 | Kiani et al. |
| 10,201,298 | B2 | 2/2019 | Al-Ali et al. |
| 10,205,272 | B2 | 2/2019 | Kiani et al. |
| 10,205,291 | B2 | 2/2019 | Scruggs et al. |
| 10,213,108 | B2 | 2/2019 | Al-Ali |
| 10,219,706 | B2 | 3/2019 | Al-Ali |
| 10,219,746 | B2 | 3/2019 | McHale et al. |
| 10,226,187 | B2 | 3/2019 | Al-Ali et al. |
| 10,226,576 | B2 | 3/2019 | Kiani |
| 10,231,657 | B2 | 3/2019 | Al-Ali et al. |
| 10,231,670 | B2 | 3/2019 | Blank et al. |
| 10,231,676 | B2 | 3/2019 | Al-Ali et al. |
| RE47,353 | E | 4/2019 | Kiani et al. |
| 10,251,585 | B2 | 4/2019 | Al-Ali et al. |
| 10,251,586 | B2 | 4/2019 | Lamego |
| 10,255,994 | B2 | 4/2019 | Sampath et al. |
| 10,258,265 | B1 | 4/2019 | Poeze et al. |
| 10,258,266 | B1 | 4/2019 | Poeze et al. |
| 10,271,748 | B2 | 4/2019 | Al-Ali |
| 10,278,626 | B2 | 5/2019 | Schurman et al. |
| 10,278,648 | B2 | 5/2019 | Al-Ali et al. |
| 10,279,247 | B2 | 5/2019 | Kiani |
| 10,292,628 | B1 | 5/2019 | Poeze et al. |
| 10,292,657 | B2 | 5/2019 | Abdul-Hafiz et al. |
| 10,292,664 | B2 | 5/2019 | Al-Ali |
| 10,299,708 | B1 | 5/2019 | Poeze et al. |
| 10,299,709 | B2 | 5/2019 | Perea et al. |
| 10,299,720 | B2 | 5/2019 | Brown et al. |
| 10,305,775 | B2 | 5/2019 | Lamego et al. |
| 10,307,111 | B2 | 6/2019 | Muhsin et al. |
| 10,325,681 | B2 | 6/2019 | Sampath et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,335,033 | B2 | 7/2019 | Al-Ali |
| 10,335,068 | B2 | 7/2019 | Poeze et al. |
| 10,335,072 | B2 | 7/2019 | Al-Ali et al. |
| 10,342,470 | B2 | 7/2019 | Al-Ali et al. |
| 10,342,487 | B2 | 7/2019 | Al-Ali et al. |
| 10,342,497 | B2 | 7/2019 | Al-Ali et al. |
| 10,349,895 | B2 | 7/2019 | Telfort et al. |
| 10,349,898 | B2 | 7/2019 | Al-Ali et al. |
| 10,354,504 | B2 | 7/2019 | Kiani et al. |
| 10,357,206 | B2 | 7/2019 | Weber et al. |
| 10,357,209 | B2 | 7/2019 | Al-Ali |
| 10,366,787 | B2 | 7/2019 | Sampath et al. |
| 10,368,787 | B2 | 8/2019 | Reichgott et al. |
| 10,376,190 | B1 | 8/2019 | Poeze et al. |
| 10,376,191 | B1 | 8/2019 | Poeze et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| RE47,882 | E | 3/2020 | Ai-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |

(56) References Cited

U.S. PATENT DOCUMENTS

D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,004,877 B2 6/2024 Kiani et al.
12,014,328 B2 6/2024 Wachman et al.
D1,036,293 S 7/2024 Al-Ali
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Ai-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin et al.
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.

(56) References Cited

U.S. PATENT DOCUMENTS 12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
12,495,967 B2 12/2025 Muhsin et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2005/0267341 A1 12/2005 Blank et al.
2006/0073719 A1 4/2006 Kiani
2006/0161054 A1 7/2006 Reuss et al.
2006/0189871 A1 8/2006 Al-Ali et al.
2007/0073116 A1 3/2007 Kiani et al.
2007/0123756 A1 5/2007 Kitajima et al.
2007/0180140 A1 8/2007 Welch et al.
2007/0244377 A1 10/2007 Cozad et al.
2007/0282478 A1 12/2007 Al-Ali et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275813 A1 11/2009 Davis
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0105854 A1 5/2011 Kiani et al.
2011/0118561 A1 5/2011 Tari et al.
2011/0125060 A1 5/2011 Telfort et al.
2011/0137297 A1 6/2011 Kiani et al.
2011/0172498 A1 7/2011 Olsen et al.
2011/0208015 A1 8/2011 Welch et al.
2011/0213212 A1 9/2011 Al-Ali
2011/0230733 A1 9/2011 Al-Ali
2011/0237969 A1 9/2011 Eckerbom et al.
2012/0046557 A1 2/2012 Kiani
2012/0088984 A1 4/2012 Al-Ali et al.
2012/0123231 A1 5/2012 O'Reilly
2012/0165629 A1 6/2012 Merritt et al.
2012/0209082 A1 8/2012 Ai-Ali
2012/0209084 A1 8/2012 Olsen et al.
2012/0226117 A1 9/2012 Lamego et al.
2012/0283524 A1 11/2012 Kiani et al.
2012/0319816 A1 12/2012 Al-Ali
2013/0023775 A1 1/2013 Lamego et al.
2013/0041591 A1 2/2013 Lamego
2013/0046204 A1 2/2013 Lamego et al.
2013/0060147 A1 3/2013 Welch et al.
2013/0096405 A1 4/2013 Garfio
2013/0096936 A1 4/2013 Sampath et al.
2013/0243021 A1 9/2013 Siskavich
2013/0253334 A1 9/2013 Al-Ali et al.
2013/0267804 A1 10/2013 Al-Ali
2013/0274572 A1 10/2013 Al-Ali et al.
2013/0296672 A1 11/2013 O'Neil et al.
2013/0296713 A1 11/2013 Al-Ali et al.
2013/0324808 A1 12/2013 Al-Ali et al.
2013/0331660 A1 12/2013 Al-Ali et al.
2013/0345921 A1 12/2013 Al-Ali et al.
2014/0012100 A1 1/2014 Al-Ali et al.
2014/0051953 A1 2/2014 Lamego et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0127137 A1 5/2014 Bellott et al.
2014/0129702 A1 5/2014 Lamego et al.
2014/0135588 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0213864 A1 7/2014 Abdul-Hafiz et al.
2014/0266790 A1 9/2014 Al-Ali et al.
2014/0275808 A1 9/2014 Poeze et al.
2014/0275835 A1 9/2014 Lamego et al.
2014/0275871 A1 9/2014 Lamego et al.
2014/0275872 A1 9/2014 Merritt et al.
2014/0276115 A1 9/2014 Dalvi et al.
2014/0288400 A1 9/2014 Diab et al.
2014/0316217 A1 10/2014 Purdon et al.
2014/0316218 A1 10/2014 Purdon et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0330099 A1 11/2014 Al-Ali et al.
2014/0336481 A1 11/2014 Shakespeare et al.
2014/0357966 A1 12/2014 Al-Ali et al.
2015/0005600 A1 1/2015 Blank et al.
2015/0011907 A1 1/2015 Purdon et al.
2015/0012231 A1 1/2015 Poeze et al.
2015/0032029 A1 1/2015 Al-Ali et al.
2015/0038859 A1 2/2015 Dalvi et al.
2015/0045637 A1 2/2015 Dalvi
2015/0051462 A1 2/2015 Olsen
2015/0073241 A1 3/2015 Lamego
2015/0080754 A1 3/2015 Purdon et al.
2015/0087936 A1 3/2015 Al-Ali et al.
2015/0094546 A1 4/2015 Al-Ali
2015/0097701 A1 4/2015 Muhsin et al.
2015/0099950 A1 4/2015 Al-Ali et al.
2015/0099951 A1 4/2015 Al-Ali et al.
2015/0099955 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0116076 A1 4/2015 Al-Ali et al.
2015/0126830 A1 5/2015 Schurman et al.
2015/0133755 A1 5/2015 Smith et al.
2015/0141781 A1 5/2015 Weber et al.
2015/0165312 A1 6/2015 Kiani
2015/0196237 A1 7/2015 Lamego
2015/0216459 A1 8/2015 Al-Ali et al.
2015/0230755 A1 8/2015 Al-Ali et al.

(56) References Cited

U.S. PATENT DOCUMENTS

2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.
2015/0351697 A1 12/2015 Weber et al.
2015/0351704 A1 12/2015 Kiani et al.
2015/0359429 A1 12/2015 Al-Ali et al.
2015/0366472 A1 12/2015 Kiani
2015/0366507 A1 12/2015 Blank et al.
2015/0374298 A1 12/2015 Al-Ali et al.
2015/0380875 A1 12/2015 Coverston et al.
2016/0000362 A1 1/2016 Diab et al.
2016/0007930 A1 1/2016 Weber et al.
2016/0029932 A1 2/2016 Al-Ali
2016/0045118 A1 2/2016 Kiani
2016/0051205 A1 2/2016 Al-Ali et al.
2016/0058338 A1 3/2016 Schurman et al.
2016/0058347 A1 3/2016 Reichgott et al.
2016/0066823 A1 3/2016 Al-Ali et al.
2016/0066824 A1 3/2016 Al-Ali et al.
2016/0066879 A1 3/2016 Telfort et al.
2016/0072429 A1 3/2016 Kiani et al.
2016/0081552 A1 3/2016 Wojtczuk et al.
2016/0095543 A1 4/2016 Telfort et al.
2016/0095548 A1 4/2016 Al-Ali et al.
2016/0103598 A1 4/2016 Al-Ali et al.
2016/0113527 A1 4/2016 Al-Ali
2016/0143548 A1 5/2016 Al-Ali
2016/0166182 A1 6/2016 Al-Ali et al.
2016/0166183 A1 6/2016 Poeze et al.
2016/0166188 A1 6/2016 Bruinsma et al.
2016/0192869 A1 7/2016 Kiani et al.
2016/0196388 A1 7/2016 Lamego
2016/0197436 A1 7/2016 Barker et al.
2016/0213281 A1 7/2016 Eckerbom et al.
2016/0228043 A1 8/2016 O'Neil et al.
2016/0233632 A1 8/2016 Scruggs et al.
2016/0234944 A1 8/2016 Schmidt et al.
2016/0270735 A1 9/2016 Diab et al.
2016/0283665 A1 9/2016 Sampath et al.
2016/0287090 A1 10/2016 Al-Ali et al.
2016/0287786 A1 10/2016 Kiani
2016/0296169 A1 10/2016 McHale et al.
2016/0310052 A1 10/2016 Al-Ali et al.
2016/0314260 A1 10/2016 Kiani
2016/0324486 A1 11/2016 Al-Ali et al.
2016/0324488 A1 11/2016 Olsen
2016/0327984 A1 11/2016 Al-Ali et al.
2016/0328528 A1 11/2016 Al-Ali et al.
2016/0331332 A1 11/2016 Al-Ali
2016/0367173 A1 12/2016 Dalvi et al.
2017/0000394 A1 1/2017 Al-Ali et al.
2017/0007134 A1 1/2017 Al-Ali et al.
2017/0007190 A1 1/2017 Al-Ali et al.
2017/0007198 A1 1/2017 Al-Ali et al.
2017/0014084 A1 1/2017 Al-Ali et al.
2017/0021099 A1 1/2017 Al-Ali et al.
2017/0024748 A1 1/2017 Haider
2017/0027456 A1 2/2017 Kinast et al.
2017/0042488 A1 2/2017 Muhsin
2017/0055847 A1 3/2017 Kiani et al.
2017/0055851 A1 3/2017 Al-Ali
2017/0055882 A1 3/2017 Al-Ali et al.
2017/0055887 A1 3/2017 Al-Ali
2017/0055896 A1 3/2017 Al-Ali
2017/0079594 A1 3/2017 Telfort et al.
2017/0086723 A1 3/2017 Al-Ali et al.
2017/0147774 A1 5/2017 Kiani
2017/0156620 A1 6/2017 Al-Ali et al.
2017/0173632 A1 6/2017 Al-Ali
2017/0187146 A1 6/2017 Kiani et al.
2017/0188919 A1 7/2017 Al-Ali et al.
2017/0196464 A1 7/2017 Jansen et al.
2017/0196470 A1 7/2017 Lamego et al.
2017/0202490 A1 7/2017 Al-Ali et al.
2017/0224262 A1 8/2017 Al-Ali
2017/0228516 A1 8/2017 Sampath et al.
2017/0245790 A1 8/2017 Al-Ali et al.
2017/0251974 A1 9/2017 Shreim et al.
2017/0251975 A1 9/2017 Shreim et al.
2017/0258403 A1 9/2017 Abdul-Hafiz et al.
2017/0311851 A1 11/2017 Schurman et al.
2017/0311891 A1 11/2017 Kiani et al.
2017/0325728 A1 11/2017 Al-Ali et al.
2017/0332976 A1 11/2017 Al-Ali
2017/0340293 A1 11/2017 Al-Ali et al.
2017/0360310 A1 12/2017 Kiani
2017/0367632 A1 12/2017 Al-Ali et al.
2018/0008146 A1 1/2018 Al-Ali et al.
2018/0013562 A1 1/2018 Haider et al.
2018/0014752 A1 1/2018 Al-Ali et al.
2018/0028124 A1 2/2018 Al-Ali et al.
2018/0055385 A1 3/2018 Al-Ali
2018/0055390 A1 3/2018 Kiani et al.
2018/0055430 A1 3/2018 Diab et al.
2018/0064381 A1 3/2018 Shakespeare et al.
2018/0069776 A1 3/2018 Lamego et al.
2018/0070867 A1 3/2018 Smith et al.
2018/0082767 A1 3/2018 Al-Ali et al.
2018/0085068 A1 3/2018 Telfort
2018/0087937 A1 3/2018 Al-Ali et al.
2018/0103874 A1 4/2018 Lee et al.
2018/0103905 A1 4/2018 Kiani
2018/0110478 A1 4/2018 Al-Ali
2018/0116575 A1 5/2018 Perea et al.
2018/0125368 A1 5/2018 Lamego et al.
2018/0125430 A1 5/2018 Al-Ali et al.
2018/0125445 A1 5/2018 Telfort et al.
2018/0130325 A1 5/2018 Kiani et al.
2018/0132769 A1 5/2018 Weber et al.
2018/0132770 A1 5/2018 Lamego
2018/0146901 A1 5/2018 Al-Ali et al.
2018/0146902 A1 5/2018 Kiani et al.
2018/0153442 A1 6/2018 Eckerbom et al.
2018/0153446 A1 6/2018 Kiani
2018/0153447 A1 6/2018 Al-Ali et al.
2018/0153448 A1 6/2018 Weber et al.
2018/0161499 A1 6/2018 Al-Ali et al.
2018/0168491 A1 6/2018 Al-Ali et al.
2018/0174679 A1 6/2018 Sampath et al.
2018/0174680 A1 6/2018 Sampath et al.
2018/0182484 A1 6/2018 Sampath et al.
2018/0184917 A1 7/2018 Kiani
2018/0192924 A1 7/2018 Al-Ali
2018/0192953 A1 7/2018 Shreim et al.
2018/0192955 A1 7/2018 Al-Ali et al.
2018/0199871 A1 7/2018 Pauley et al.
2018/0206795 A1 7/2018 Al-Ali
2018/0206815 A1 7/2018 Telfort
2018/0213583 A1 7/2018 Al-Ali
2018/0214031 A1 8/2018 Kiani et al.
2018/0214090 A1 8/2018 Al-Ali et al.
2018/0218792 A1 8/2018 Muhsin et al.
2018/0225960 A1 8/2018 Al-Ali et al.
2018/0238718 A1 8/2018 Dalvi
2018/0242853 A1 8/2018 Al-Ali
2018/0242921 A1 8/2018 Muhsin et al.
2018/0242923 A1 8/2018 Al-Ali et al.
2018/0242924 A1 8/2018 Barker et al.
2018/0242926 A1 8/2018 Muhsin et al.
2018/0247353 A1 8/2018 Al-Ali et al.
2018/0247712 A1 8/2018 Muhsin et al.
2018/0249933 A1 9/2018 Schurman et al.
2018/0253947 A1 9/2018 Muhsin et al.
2018/0256087 A1 9/2018 Al-Ali et al.
2018/0256113 A1 9/2018 Weber et al.
2018/0285094 A1 10/2018 Housel et al.
2018/0289325 A1 10/2018 Poeze et al.
2018/0289337 A1 10/2018 Al-Ali et al.
2018/0296161 A1 10/2018 Shreim et al.
2018/0300919 A1 10/2018 Muhsin et al.
2018/0310822 A1 11/2018 Indorf et al.
2018/0310823 A1 11/2018 Al-Ali et al.

(56) References Cited

U.S. PATENT DOCUMENTS

2018/0317826 A1 11/2018 Muhsin et al.
2018/0317841 A1 11/2018 Novak, Jr.
2018/0333055 A1 11/2018 Lamego et al.
2018/0333087 A1 11/2018 Ai-Ali
2019/0000317 A1 1/2019 Muhsin et al.
2019/0000362 A1 1/2019 Kiani et al.
2019/0015023 A1 1/2019 Monfre
2019/0021638 A1 1/2019 Al-Ali et al.
2019/0029574 A1 1/2019 Schurman et al.
2019/0029578 A1 1/2019 Al-Ali et al.
2019/0038143 A1 2/2019 Al-Ali
2019/0058280 A1 2/2019 Al-Ali et al.
2019/0058281 A1 2/2019 Al-Ali et al.
2019/0069813 A1 3/2019 Al-Ali
2019/0069814 A1 3/2019 Al-Ali
2019/0076028 A1 3/2019 Al-Ali et al.
2019/0082979 A1 3/2019 Al-Ali et al.
2019/0090748 A1 3/2019 Al-Ali
2019/0090760 A1 3/2019 Kinast et al.
2019/0090764 A1 3/2019 Al-Ali
2019/0104973 A1 4/2019 Poeze et al.
2019/0110719 A1 4/2019 Poeze et al.
2019/0117070 A1 4/2019 Muhsin et al.
2019/0117139 A1 4/2019 Al-Ali et al.
2019/0117140 A1 4/2019 Al-Ali et al.
2019/0117141 A1 4/2019 Al-Ali
2019/0117930 A1 4/2019 Al-Ali
2019/0122763 A1 4/2019 Sampath et al.
2019/0133525 A1 5/2019 Al-Ali et al.
2019/0142283 A1 5/2019 Lamego et al.
2019/0142344 A1 5/2019 Telfort et al.
2019/0150800 A1 5/2019 Poeze et al.
2019/0150856 A1 5/2019 Kiani et al.
2019/0167161 A1 6/2019 Al-Ali et al.
2019/0175019 A1 6/2019 Al-Ali et al.
2019/0192076 A1 6/2019 McHale et al.
2019/0200941 A1 7/2019 Chandran et al.
2019/0201623 A1 7/2019 Kiani
2019/0209025 A1 7/2019 Al-Ali
2019/0214778 A1 7/2019 Scruggs et al.
2019/0216319 A1 7/2019 Poeze et al.
2019/0216379 A1 7/2019 Al-Ali et al.
2019/0221966 A1 7/2019 Kiani et al.
2019/0223804 A1 7/2019 Blank et al.
2019/0231199 A1 8/2019 Al-Ali et al.
2019/0231241 A1 8/2019 Al-Ali et al.
2019/0231270 A1 8/2019 Abdul-Hafiz et al.
2019/0239787 A1 8/2019 Pauley et al.
2019/0239824 A1 8/2019 Muhsin et al.
2019/0254578 A1 8/2019 Lamego
2019/0320906 A1 10/2019 Olsen
2019/0374139 A1 12/2019 Kiani et al.
2019/0374713 A1 12/2019 Kiani et al.
2020/0060869 A1 2/2020 Telfort et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0039707 A1 2/2022 Sharma et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Ai-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen

(56) References Cited

U.S. PATENT DOCUMENTS

| | | | |
|---|---|---|---|
| 2025/0255764 | A1 | 8/2025 | Stead |
| 2025/0278512 | A1 | 9/2025 | Koo et al. |
| 2025/0281059 | A1 | 9/2025 | Avendano |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |

* cited by examiner 80
704
714
700
718
116
112
113
110
716
114
100
126
120
123
122
124
125
702
712

402
404
410
412
414
420
430
412
414
410
404
402

302
304
320
330
304
302

OPTICAL SENSOR TAPE

INCORPORATION BY REFERENCE TO ANY PRIORITY APPLICATIONS

The present application is a continuation of U.S. patent application Ser. No. 17/518,427, filed Nov. 3, 2021, and titled "OPTICAL SENSOR TAPE", which is a continuation of U.S. patent application Ser. No. 15/582,082, filed Apr. 28, 2017, and titled "OPTICAL SENSOR TAPE", and issued as U.S. Pat. No. 11,191,484, which claims benefit of priority to U.S. Provisional Application No. 62/329,451, filed Apr. 29, 2016. The disclosure of each of these applications is incorporated herein in its entirety for all purposes. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to low-noise optical probes which may be used to sense optical energy passed through a medium to determine the characteristics of the medium.

BACKGROUND

Pulse oximetry—a noninvasive, widely accepted form of oximetry—relies on a sensor attached externally to a patient to output signals indicative of various physiological parameters, such as a patient's constituents or analytes, including, for example, oxygen saturation (SpO2), hemoglobin (Hb), blood pressure (BP), pulse rate (PR), perfusion index (PI), Pleth Variable Index (PVI), carbon monoxide saturation (HbCO), methemoglobin saturation (HbMet), fractional saturations, total hematocrit, billirubins, or the like. As such a pulse oximeter is one of a variety of patient monitors that help provide monitoring of a patient's physiological characteristics.

Pulse oximeters are available from Masimo Corporation ("Masimo") of Irvine, California. Moreover, some exemplary portable and other oximeters are disclosed in at least U.S. Pat. Nos. 6,770,028, 6,658,276, 6,157,850, 6,002,952, and 5,769,785, which are owned by Masimo, and are incorporated by reference herein. Such oximeters have gained rapid acceptance in a wide variety of medical applications, including surgical wards, intensive care and neonatal units, general wards, home care, physical training, and virtually all types of monitoring scenarios.

SUMMARY

A pulse oximeter sensor generally includes one or more energy emission devices, such as specific wavelength emitting light emitting diodes ("LED"), and one or more energy detection devices. The sensor is generally attached to a measurement site such as a patient's finger, toe, ear, ankle, or the like. An attachment mechanism positions the emitters and detector, collectively called an optical probe, proximal to the measurement site such that the emitters project energy into the tissue, blood vessels, and capillaries of the measurement site, which in turn attenuate the energy. The detector then detects that attenuated energy. The detector communicates at least one signal indicative of the detected attenuated energy to one or more digital signal processors, for calculating, among other things, one or more physiological parameters of the measurement site.

The present disclosure discloses an improved sensor tape for securing a non-invasive optical sensor, such as a pulse oximeter sensor, to a surface of a medium for taking noninvasive measurement of characteristics of the medium. The sensor tapes of the present disclosure can increase contact surface between the surface of the medium and an adhesive side of the tape in order to increase tape adhesion to the medium and to reduce motion-induced noise. The sensor tapes of the present disclosure can be disposable and lost cost. The sensor tapes of the present disclosure can also be manufactured in a manner that maximizes the amount of material used so as to keep material cost low.

One type of disposable sensor uses an "L"-shaped configuration. This type of configuration is generally used for infant patients so that the sensor can be used in a variety of measurement sites on the infant. As the tape is applied to the patient, the tape is often wound around a patient measurement site and later portions of the tape are adhered to the back of previous portions of the tape. Although the present disclosure is described mainly with respect to an L-shaped tape sensor, the embodiments of sensor tapes in this disclosure are not limited to being used with an L-shaped sensor, but are applicable to any type of sensor shapes and configurations.

In some embodiments, a sensor tape for securing a non-invasive optical sensor to a surface of a medium for taking physiological measurements is disclosed. The sensor tape can comprise a first end with a first width, a second end with a second width, the second width greater than the first width, and a flexible tape portion between the first and second ends, the tape portion including an adhesive surface and a non-adhesive surface. The sensor tape can be tapered such that a width of the tape decreases gradually from the second end to the first end. The sensor tape can further comprise a first portion and a second portion, the first portion having a width substantially the same as the first width, the second portion having a width substantially the same as the second width. The first portion can transition to the second portion in a step-like change. The sensor tape can comprise a sloped transition between the first portion and the second portion. The first and second portions can have substantially the same length.

In some embodiments, a sensor assembly for measuring characteristics of the medium is disclosed. The sensor assembly can comprise a sensor having a detector arm and a connector arm, the detector arm and the connector arm forming an L-shape, and a sensor tape configured to position and secure the sensor to a surface of the medium, the sensor tape having a first end with a first width, a second end with a second width, the second width greater than the first width, the sensor tape further having a flexible tape portion between the first and second ends, the tape portion having an adhesive surface and a non-adhesive surface, and the sensor tape substantially covering the detector arm. The detector arm can comprise an emitter and a detector. The second end of the sensor tape can be closer to the sensor than the first end of the sensor tape. The first end of the sensor tape is closer to the sensor than the second end of the sensor tape. The sensor tape can be tapered such that a width of the tape decreases gradually from the second end to the first end. The sensor tape can further comprise a first portion and a second portion, the first portion having a width substantially the same as the first width, the second portion having a width substantially the same as the second width. The first portion can transition to the second portion in a step-like change. The sensor tape can comprise a sloped transition between the first portion and the second portion. The first and second portions can have substantially the same length.

In some embodiments, a sensor tape for positioning and securing a noninvasive L-shaped sensor to a surface of a medium for measuring characteristics of the medium is disclosed, the L-shaped sensor comprising a detector arm and a connector arm, the detector and connector arms being perpendicular to each other and forming a substantially L-shape, the detector arm comprising an optical emitter and an optical detector. The sensor assembly can comprise a first portion of flexible tape having an adhesive surface and a non-adhesive surface, the first portion having first and second ends, the adhesive surface of the first portion configured to cover the detector arm of the L-shaped sensor and attach to a measurement site, the first portion configured to be substantially parallel to the detector arm; and a second portion of flexible tape having an adhesive surface and a non-adhesive surface, the second portion having first and second ends, the adhesive surface of the second portion configured to attach to a measurement site; wherein the first end of the first portion is connected to the second portion between the first and second ends of the second portion such that the first and second portions are configured to independently wrap around a measurement site. The optical emitter of the detector arm can be configured to be at or near the first end of the first portion and the optical detector is configured to be between the first and second ends of the first portion. The first portion can be longer than the second portion such that the second end of the first portion extends beyond the second end of the second portion. The first and second portions can form an integral piece of sensor tape. The second portion can be configured to cover a portion of the connector arm of the L-shaped sensor. The first and second portions can be mechanically decoupled. The sensor tape can be configured to be placed across a joint of a digit such that the first and second portions are placed on opposite sides of the joint.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
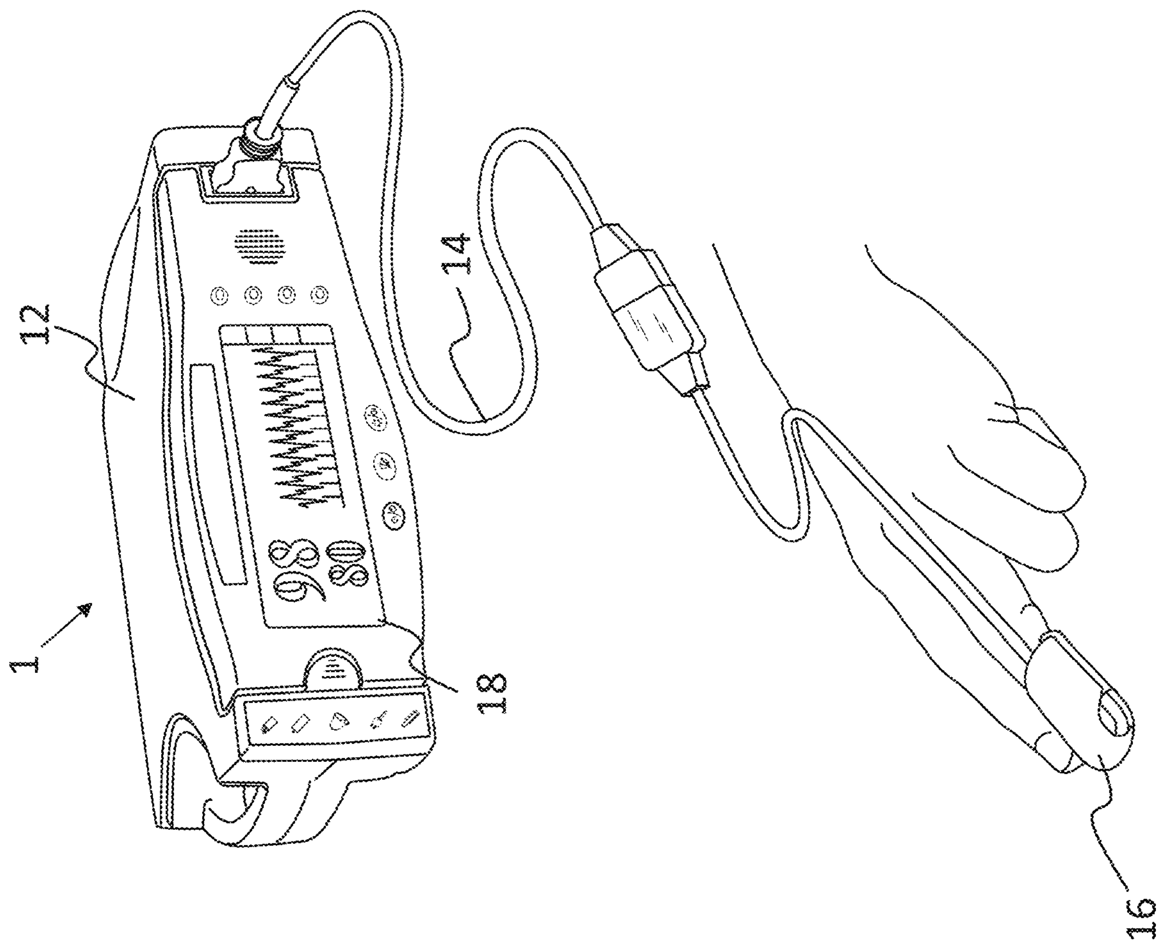
FIG. 1 illustrates a perspective view of an embodiment of a patient monitor system according to the disclosure.

Turning to FIG. 1, an embodiment of a multi-parameter patient monitor system 1 is illustrated. The patient monitor system 1 includes a patient monitor 12 attached to a sensor 16 by a cable 14. The sensor can monitor various physiological data of a patient and send signals indicative of the parameters to the patient monitor 12 for processing. The patient monitor can include a display 18 that is capable of displaying readings of various monitored patient parameters, including one or more graphs. The display 18 may be a liquid crystal display (LCD), a cathode ray tube (CRT), a plasma screen, a Light Emitting Diode (LED) screen, Organic Light Emitting Diode (OLED) screen, or any other suitable display. The patient monitor system 1 may monitor oxygen saturation ($SpO_2$), perfusion index (PI), pulse rate (PR), hemoglobin count, and other parameters described above. Typically, the patient monitor 12 can also include user control interfaces and a speaker for audible alerts. The patient monitor 12 can also include inputs from other devices, such as, an EKG machine, an ECG machine, a respirator, a ventilator, a blood pressure monitor, a capnograph, combinations of the same, or the like. The sensor 16 can be attached to a measurement site with an attachment mechanism. Non-limiting examples of a measurement site can include a fingertip, arm, leg, or foot of a patient, such as a neonatal patient. The attachment mechanism can be disposable, including, for example, adhesive tapes, hook and loop, magnets or other disposable attachments as described herein.

Figure 2:
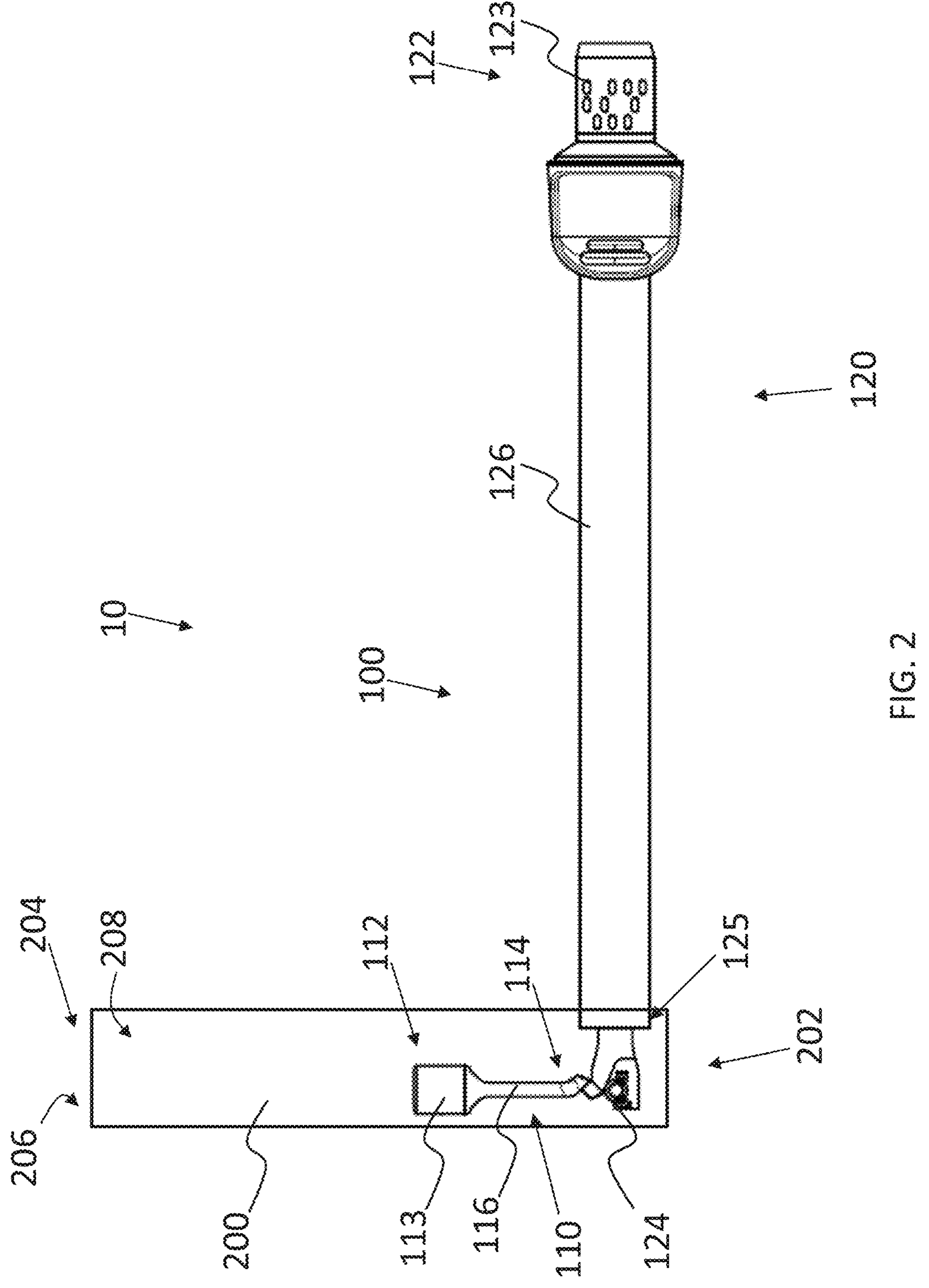
FIG. 2 illustrates a top view of an embodiment of a sensor assembly including an L-shaped sensor and a sensor tape.

FIG. 2 shows a top view of an embodiment of a sensor assembly 10 including an L-shaped sensor 100 and a sensor tape 200. The sensor 100 can have a detector arm 110 and a connector arm 120 forming a substantially L-shape. The detector arm 110 can have a free end 112 on and a fixed end 114. The detector arm 110 can have a detector 113 at or near the free end 112. The detector arm 110 can have an emitter 124 at or near the fixed end 114. The emitter 124 can be located anywhere between the free and fixed ends 112, 114. The detector 113 and the emitter 124 locations can be swapped so that the emitter 124 is located at or near the free end 112 and the detector 113 is located at or near the fixed end 114. The detector 112 and the fixed end 114 can be connected by a neck portion 116. The neck portion 116 may vary in length depending on the patient's anatomy so that the detector 112 and an emitter 124 can be positioned on opposite sides of the patient's anatomy. In some embodiments, the emitter 124 can include one or more LEDs. In some embodiments, the detector 112 can include one or more photodetectors. The fixed end 114 can be connected to the connector arm 120. The connector arm 120 can have a cable connector 123 on a free end 122. The connector arm 120 can have a fixed end 125 opposite the free end 122 along a length of the connector arm 120 for connecting to the fixed end 114 of the detector arm 110. The connector arm 120 can also include a flexible foam strip 126 extending between the cable connector 123 and the emitter 124. The cable connector 122, the emitter 124, and the detector 112 can be electrically connected to form a portion of an electrical circuit. The flexible foam strip 126 can protect the electrical circuit. The electrical circuit can be configured to attach to other electrical components, such as a resistor and/or an electrically erasable programmable read-only memory ("EEPROM"), which are not shown in the figures for clarity. The cable connector 123 can be operably coupled to a sensor cable (see FIGS. 11A-B and 14A-B), which can be plugged into a variety of patient monitors, such as the patient monitor 12 of FIG. 1, or pulse oximeters or any other multi-parameter monitors for providing noninvasive physiological measurements. Methods of manufacturing the L-shaped sensor is not limiting. In some embodiments, the L-shaped sensor 100 can be manufactured as a straight arm and be folded into the L-shape. In other embodiments, the fixed end 114 of the detector arm 110 and the fixed end 125 of the connector arm 120 can be attached mechanically, welded or affixed using adhesives. Additional details regarding the L-shaped sensor and other features can be found in U.S. application Ser. No. 15/017,505, filed Feb. 5, 2016, which is hereby incorporated by reference in its entirety and should be considered a part of this specification. The L-shaped sensor can be used for infant patients as the flexible connector arm 120 can give a caregiver more flexibility for connecting the sensor to various locations on an infant or neonatal patient. Although the present disclosure is described mainly with reference to the L-shaped sensor, the embodiments of sensor tapes described herein are not limited to being used with an L-shaped sensor, but are applicable to any suitable type of sensors. For example, the tapes disclosed herein can be used for securing sensors onto a fingertip or arm of an adult patient.

With continued reference to FIG. 2, the sensor tape 200 can cover the detector arm 110 of the L-shaped sensor 100. The sensor tape 200 can have a sensor end 202 and a free end 204. The sensor end 202 can be proximate the emitter 124. The sensor tape 200 can extend along a length of the detector arm 110, past the detector 113, and terminate at the free end 204. The sensor tape 200 can be substantially longer than the detector arm 110 so as to wrap around the patient's anatomy in more than one loop. The length of the sensor tape 200 can depend on the dimension of the patient's anatomy to which the sensor tape 200 can be applied. The sensor tape 200 can have an adhesive side 206 and a non-adhesive side 208. Materials for making the adhesive side 206 and the non-adhesive side 208 are not limiting. In some embodiments, the detector arm 110 can be sandwiched between the adhesive side 206 and the non-adhesive side 208. In some embodiments, the detector arm 110 can be positioned beneath or immediately adjacent to the adhesive side 206. The sensor tape 200 can have a rectangular shape with a substantially uniform first width and a length. During use, the neck portion 116 of the detector arm can be wrapped around a patient's anatomy, such as a foot, a hand, a finger, or a toe, so that the emitter 124 and the detector 112 are on opposite sides of the patient's anatomy. For example, the emitter 124 can be on a patient's palm and the detector 112 can be on a back of the same hand opposite the emitter 124. After the emitter 124 and the detector 112 have been positioned, the sensor tape 200 can continue to be wrapped around the patient's anatomy from the sensor end 202 to the free end 204. An initial length of the adhesive side 206 of the sensor tape 200 can directly contact the patient's skin, resulting in a contact area. After the sensor tape 200 has made one loop around the patient's anatomy, a remaining length of the adhesive side 206 of the sensor tape 200 can contact substantially the non-adhesive side 208 of the tape instead of the patient's skin. The sensor tape 200 advantageously reduces motion-induced noise by firmly positioning and securing the emitter 124 and the detector 112 to the patient's skin, thereby minimizing movements of the sensor 100 relative to the patient due to patient's movement. Bonding formed between the remaining length of the adhesive side 206 and the non-adhesive side 208 can prevent the sensor tape 200 from loosening, thereby facilitating the secure attachment of the sensor tape 200 with the emitter 124 and the detector 113 to the patient at or near the measurement site. The L-shaped sensor 100 is typically attached to the measurement site such that the connector arm 120 extends along the patient's anatomy, such as the patient's finger, hand, toe, foot, arm, or leg. The patient's anatomy can provide support to the connector arm 120 or protect the connector arm 120 from being pulled during use of the sensor. In some instances, the caregiver or user can attach the L-shaped sensor 100 to the measurement site such that the connector arm 120 extends away from the patient's anatomy. In these instances, the connector arm 120 can be tangling from the measurement site and prone to pulling. Pulling on the connector arm 120 can cause the sensor 100 and the sensor tape 200 be yanked away from the patient's skin.

Various embodiments of sensor tapes that can improve securement of the L-shaped sensor 100 to the measurement site will now be described. The improved sensor tapes described herein can minimize or eliminate sliding between the detector arm 110 of the sensor 100 and the patient's skin during use of the sensor 100. The sliding can be caused by the patient's movement or due to pulling on the connector arm 120 or the sensor cable. The improved sensor tapes described herein can provide sufficient bonding between the tape and the patient's skin such that even when the L-shaped sensor 100 is attached with the connector arm 120 extending away from the patient's anatomy, the improved sensor tape and the sensor 100 can stay attached to the patient's skin.

Tapered Sensor Tapes

Figure 3:
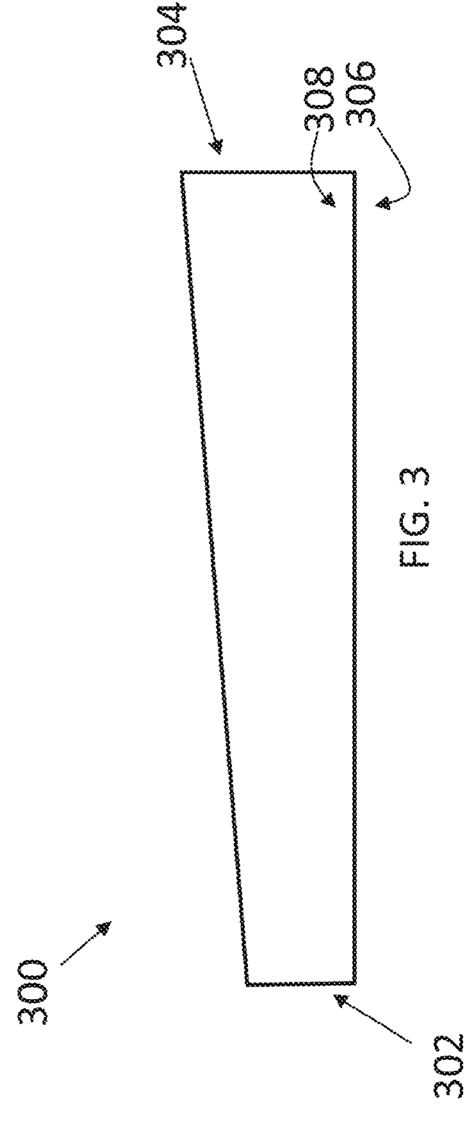
FIG. 3 illustrates a top view of an embodiment of a sensor tape.

FIG. 3 shows a top view of a tapered sensor tape 300. The sensor tape 300 can have features of the sensor tape 200 except as described below. Accordingly, features of the sensor tape 300 can be incorporated into features of the sensor tape 200 and features of the sensor tape 200 can be incorporated into features of the sensor tape 300. The sensor tape 300 can have a first end 302 and a second end 304. The sensor tape 300 can have a first width at the first end 302. The sensor tape 300 can have a second width at the second end 304. As shown in FIG. 3, the second width is greater than the first width. The first width of the sensor tape 300 can be substantially the same as the first width of the sensor tape 200 as shown in FIG. 2. Accordingly, the sensor tape 300 tapers, for example, gradually tapers, from the second end 304 to the first end 302. The geometry between the first end 302 and second end 304 is not limiting. For example, the sensor tape 300 can have wavy edges instead of straight edges on any of the four sides. The sensor tape 300 can also have an adhesive side 306 and a non-adhesive side 308.

Figure 4A:
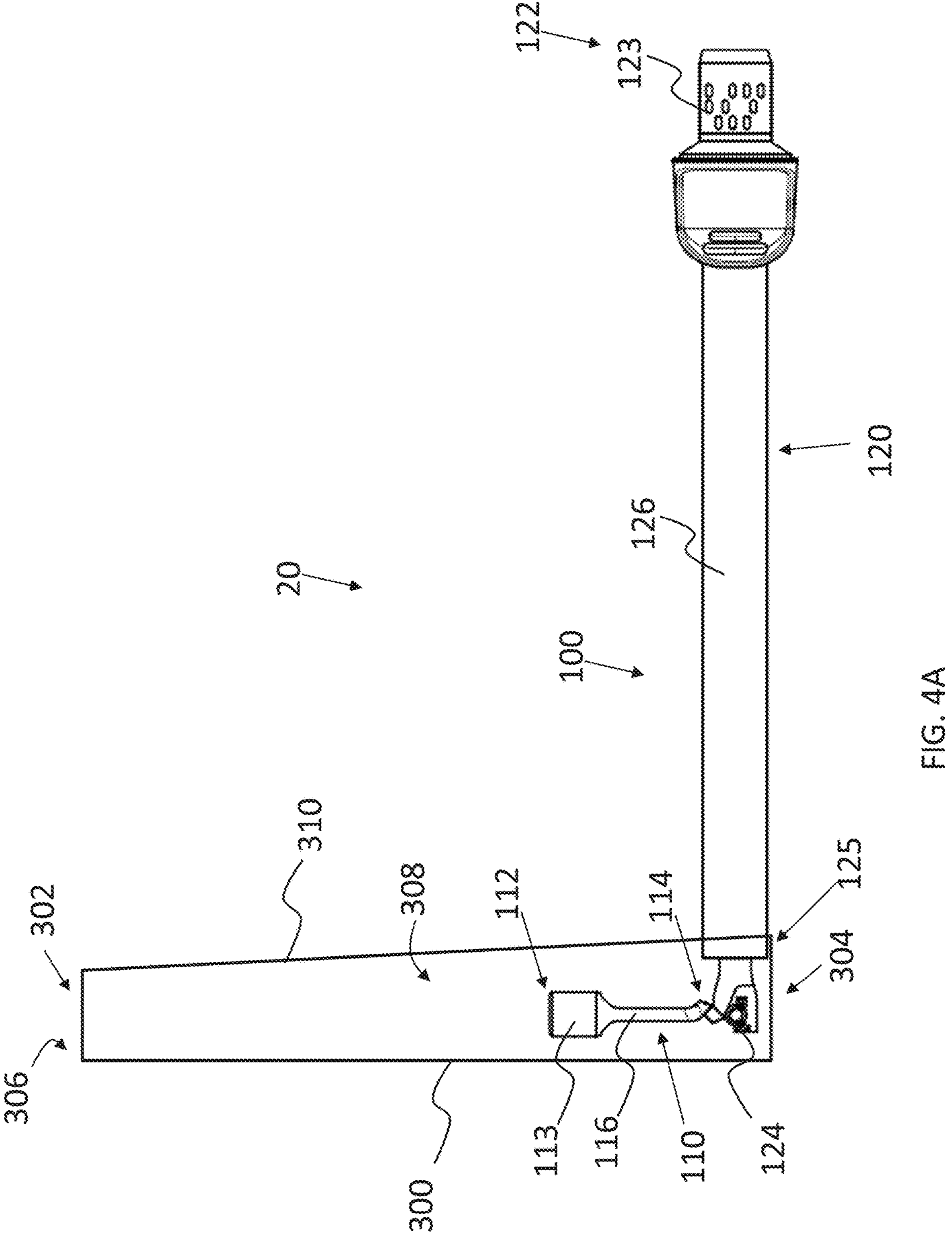
FIG. 4A illustrates a top view of an embodiment of a sensor assembly including the L-shaped sensor of FIG. 2 and the sensor tape of FIG. 3.
Figure 4B:
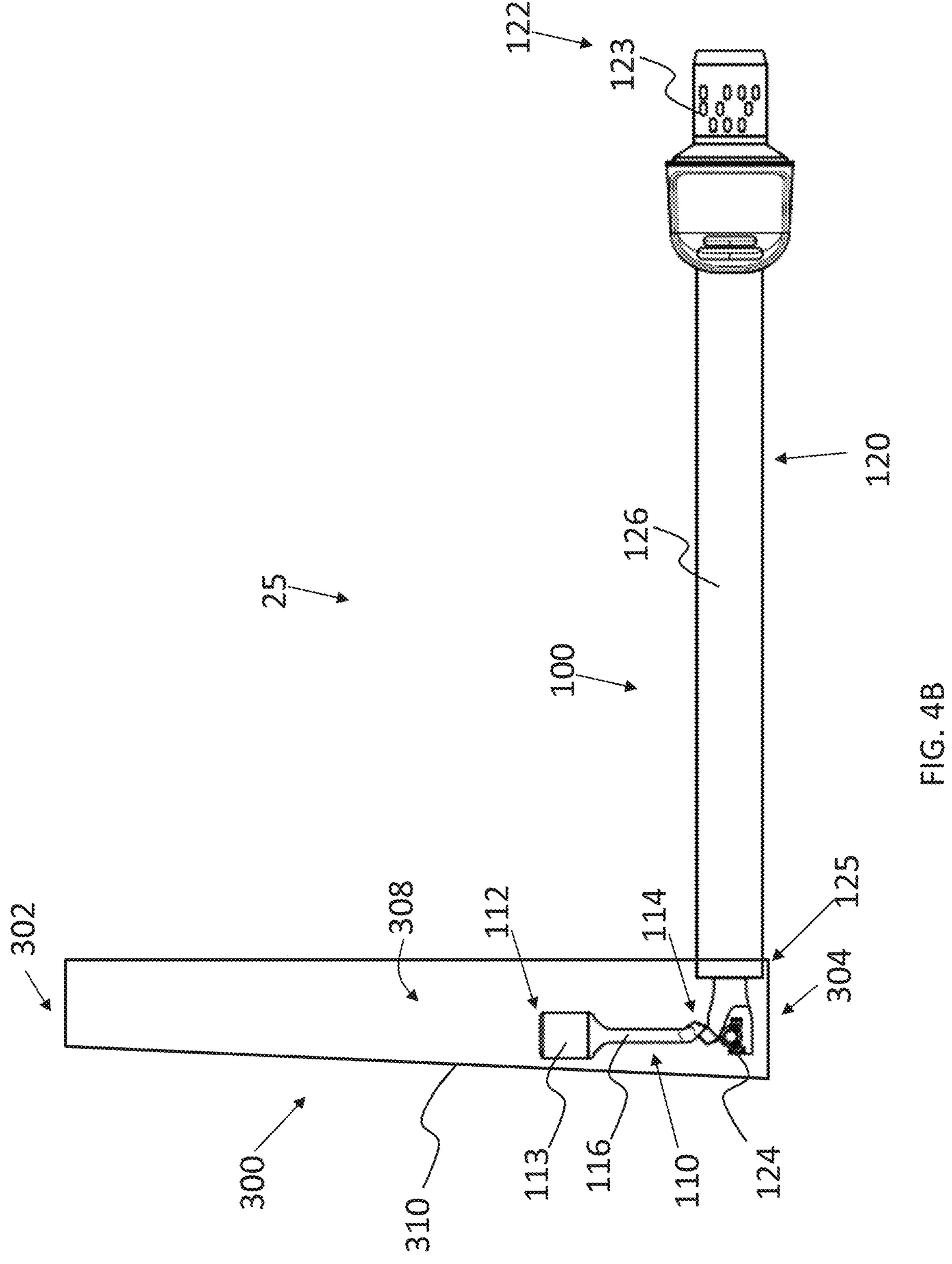
FIG. 4B illustrates a top view of an embodiment of a sensor assembly including the L-shaped sensor of FIG. 2 and the sensor tape of FIG. 3.

FIGS. 4A-B illustrate embodiments of sensor assembly 20, 25 including the L-shaped sensor 100 and the tapered sensor tape 300. As shown in FIGS. 4A-B, the second end 304 of the sensor tape 300 can be proximate the emitter 124. The sensor tap 300 can extend along a length of the detector arm 110, past the detector 113, and terminate at the first end 302. The sensor tape 300 can be substantially parallel to the detector arm 110. The second width and a length of the sensor tape 300 are sufficient to cover the detector arm 110. The sensor tape 300 can be substantially longer than the length of the detector arm 110. In FIG. 4A, the tapered side 310 of the sensor tape 300 can be closer to the connector arm 120 than the non-tapered opposite side. In FIG. 4B, the tapered side 310 can be further away from the connector arm 120 than the non-tapered opposite side. During use, the sensor tape 300 can be wrapped around the patient's anatomy from the second end 304 to the first end 302. An initial length of the adhesive side 306 of the sensor tape 300 can directly contact the patient's skin, resulting in a contact area. The contact area between the sensor tape 300 and the patient's skin is greater than the contact area between the sensor tape 200 and the patient's skin, because the sensor tape 300 is wider near the fixed end 114 of the detector arm 110 of the sensor 100 in the sensor assembly 20, 25 than the sensor tape 200 in the sensor assembly 10. The sensor tape 300 in the sensor assembly 20, 25 can advantageously provide greater contact area and thus better securement between the sensor assembly and the patient's skin, thereby further minimizing movements of the sensor 100 relative to the patient's skin. Further, as described above, after the sensor tape 300 has made one loop around the patient's anatomy, a remaining length of the adhesive side 306 can contact substantially the non-adhesive side 308 of the tape instead of the patient's skin. Accordingly, the sensor tape 300 can provide better securement of the L-shaped sensor 100 by providing a greater contact area between the adhesive side 306 of the sensor tape 300 with the patient skin than the sensor tape 200, but without requiring a significant increase in use of tape materials due to the tapering of the sensor tape 300.

Figure 5A:
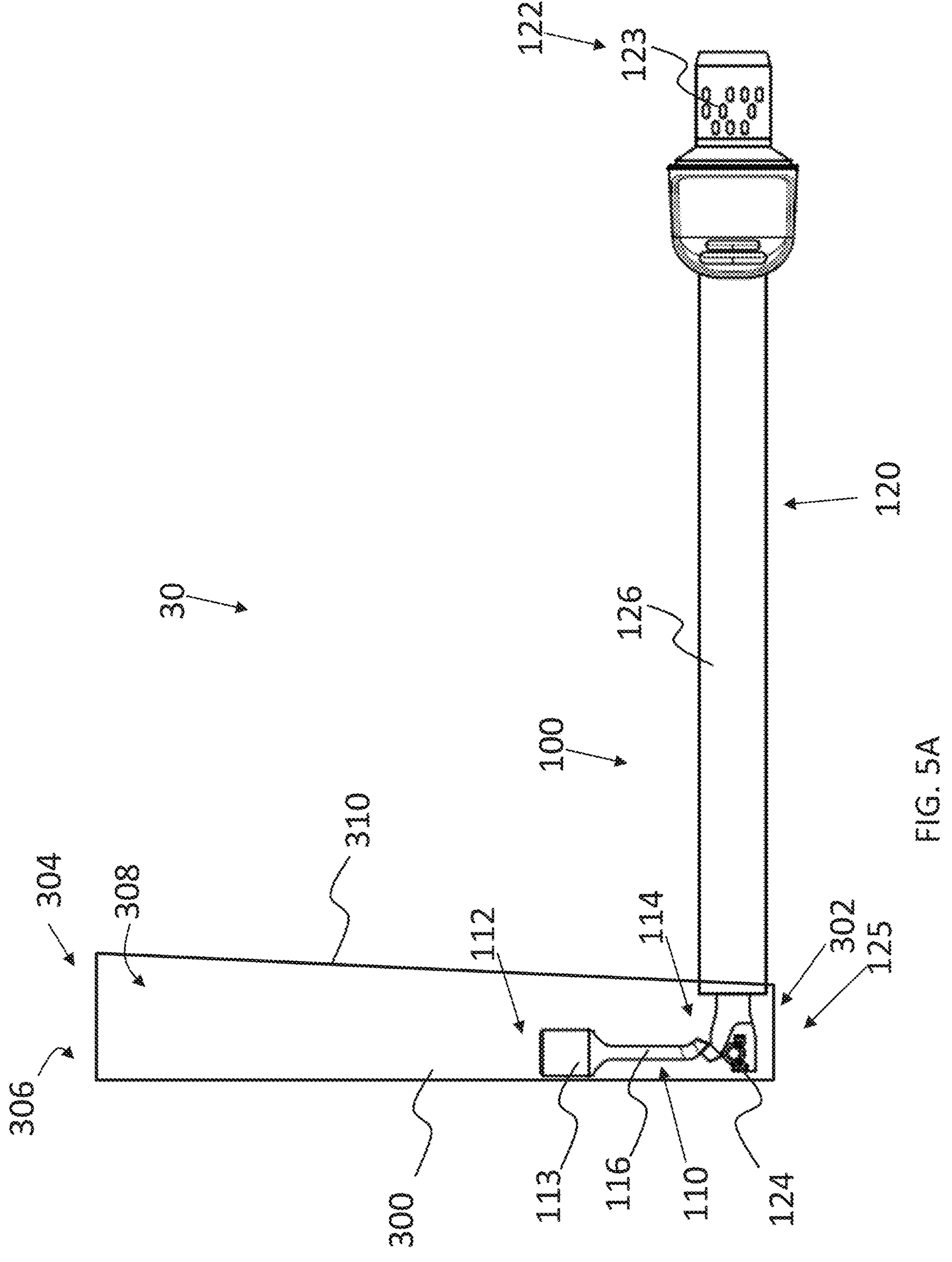
FIG. 5A illustrates a top view of an embodiment of a sensor assembly including the L-shaped sensor of FIG. 2 and the sensor tape of FIG. 3.
Figure 5B:
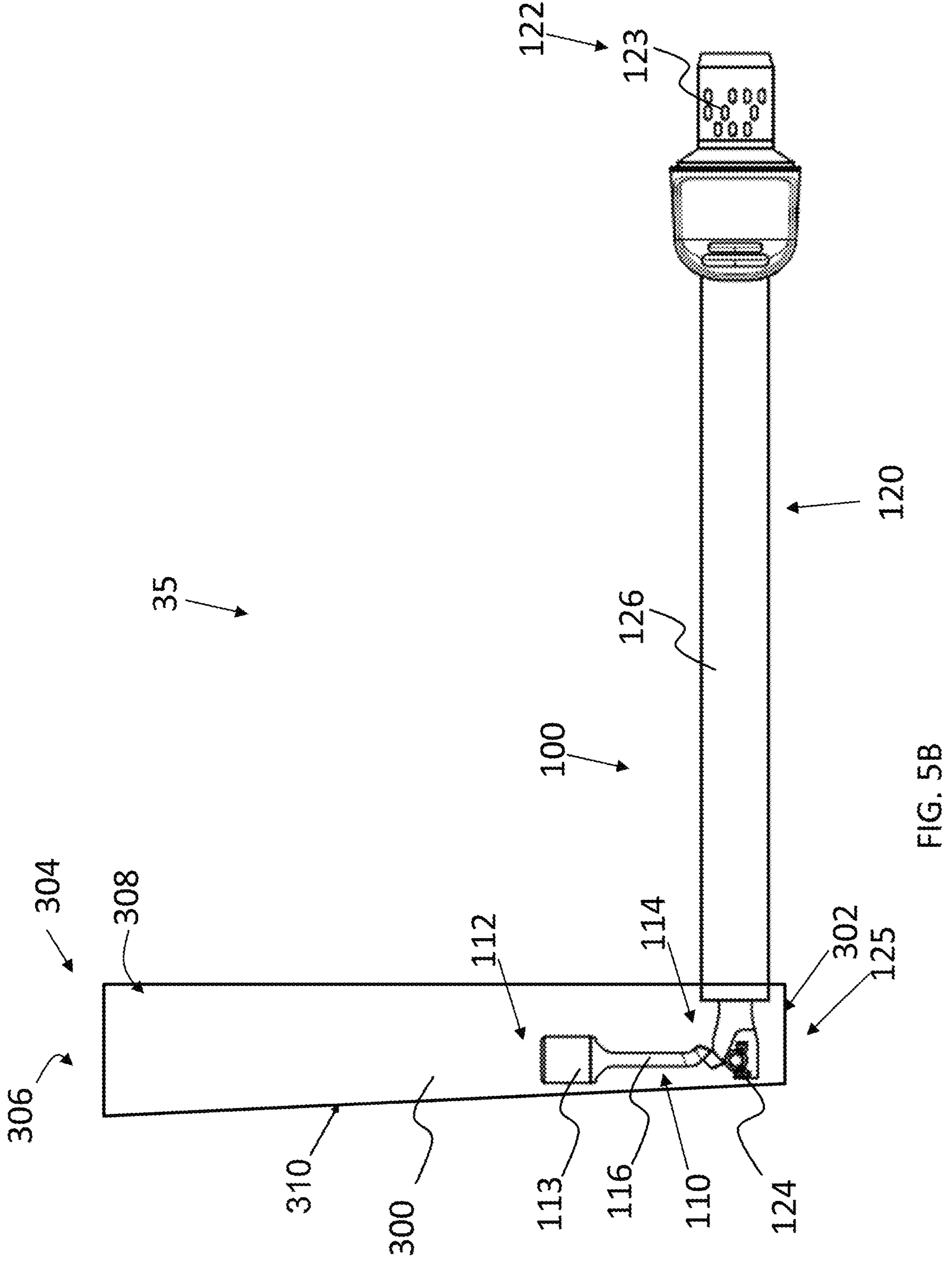
FIG. 5B illustrates a top view of an embodiment of a sensor assembly including the L-shaped sensor of FIG. 2 and the sensor tape of FIG. 3.

FIGS. 5A-B illustrate embodiments of sensor assembly 30, 35 including the L-shaped sensor 100 and the tapered sensor tape 300. As show in FIGS. 5A-B, the first end 302 of the sensor tape 300 can be proximate the emitter 124. The sensor tape 300 can extend along a length of the detector arm 110, past the detector 112, and terminate at the second end 304. The sensor tape 300 can be substantially parallel to the detector arm 110. The first width of the sensor tape 300 can be sufficient to cover the detector arm 110. In FIG. 5A, the tapered side 310 of the sensor tape 300 can be closer to the connector arm 120 than the non-tapered opposite side. In FIG. 5B, the tapered side 310 can be further away from the connector arm 120 than the non-tapered opposite side. During use, after the sensor tape 300 has made a first loop around the patient's anatomy, a remaining length of the adhesive side 306 can contact partially the non-adhesive side 308 of the first loop and partially the patient's skin because the sensor tape 300 becomes increasing wider from the fixed end 114 to the free end 112 of the detector arm 110. Specifically, the sensor tape 300 is narrower near the emitter 124 and gradually widens toward the detector 112. As a result, after each loop of the sensor tape 300 around the patient's anatomy, the adhesive side 306 of the sensor tape 300 is wider than the non-adhesive side 308 of the previous loop. The wider adhesive side 306 can then contact the skin not covered by the non-adhesive side 308 of the previous loop. The total contact area between the sensor tape 300 of the sensor assembly 30, 35 and the patient's skin is thus higher than the contact area between the sensor tape 200 and the patient's skin. In addition, the narrow first end 302 of the tape 300 can be easier to place on the finger to align the emitter 124 and the detector 113 before the wider second end 304 can wrap the detector arm 110 and the narrower part of the sensor tape 300 in place. The wider second end 304 can attach a portion of the connector arm 120 to the patient's skin. The sensor assembly 30, 35 can therefore better position and secure the sensor 100 to the patient's skin than the sensor tape 200, while not requiring a significant increase in use of tape materials due to the tapering of the sensor tape 300.

Stepped Sensor Tapes

Figure 6:
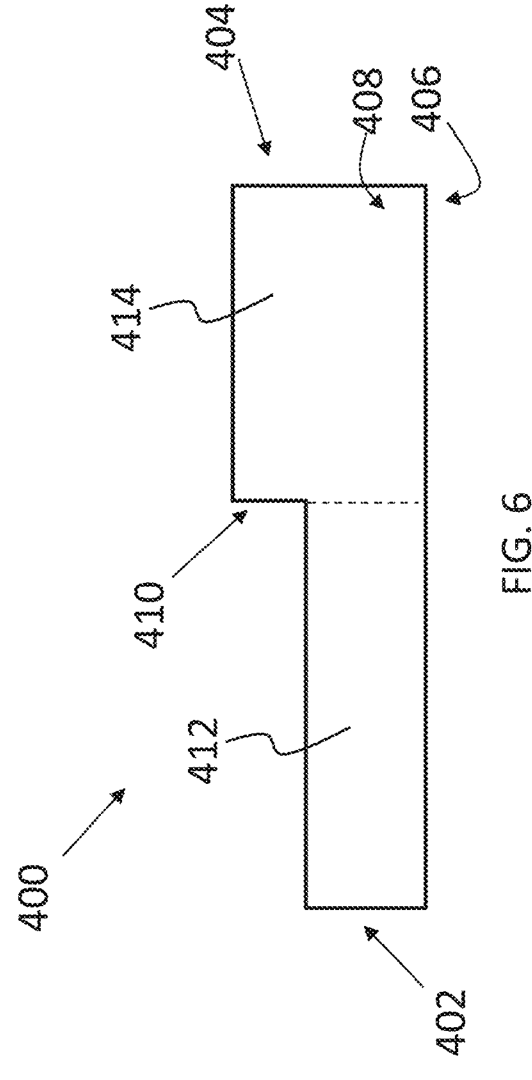
FIG. 6 illustrates a top view of an embodiment of a sensor tape.

FIG. 6 illustrates a top view of a stepped sensor tape 400. The sensor tape 400 can have features of the sensor tapes 200, 300 except as described below. Accordingly, features of the sensor tape 400 can be incorporated into features of the sensor tapes 200, 300 and features of the sensor tapes 200, 300 can be incorporated into features of the sensor tape 400. The sensor tape 400 can have a first end 402 and a second end 404. The sensor tape 400 can have a first width at the first end 402. The sensor tape 400 can have a second width at the second end 404. As show in FIG. 6, the second width is greater than the first width. The first width of the sensor tape 400 can be substantially the same as the first widths of the sensor tapes 200, 300. The sensor tape 400 can transition from the first width to the second width in a step-like change 410. The step-like transition 410 can be at a location between the first end 402 and the second end 404. The step-like transition 410 can separate the sensor tape 400 into a first portion 412 and a second portion 414. The exact geometries of the first portion 412 and the second portion 414 are not limiting. For example, at least one of the first portion 412 and the second portion 414 can have wavy edges on any sides. The step-like change 410 can be on one side or both sides along the length of the sensor tape 400. The sensor tape 400 can have an adhesive side 406 and a non-adhesive side 408.

Figure 7A:
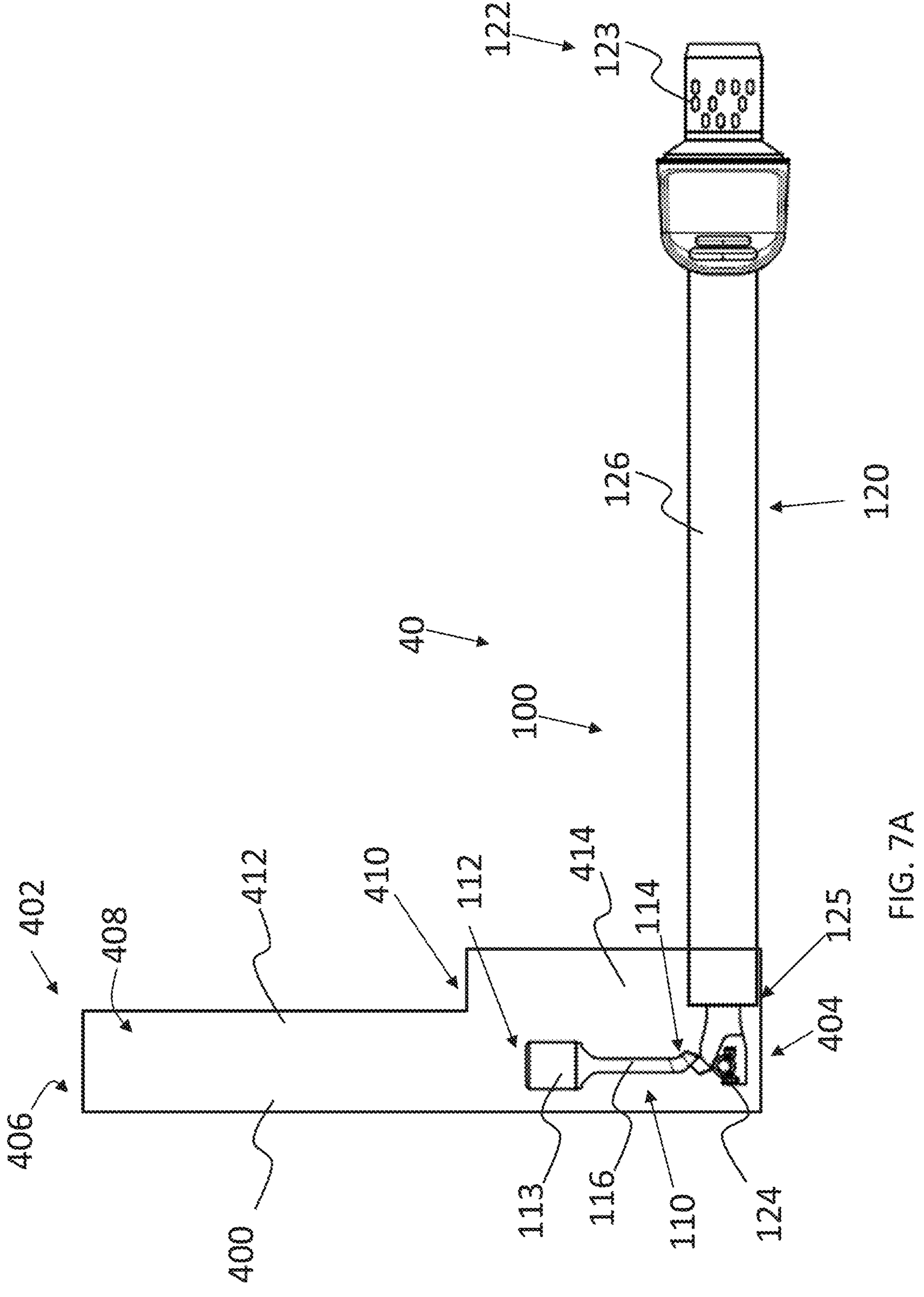
FIG. 7A illustrates a top view of an embodiment of a sensor assembly including the L-shaped sensor of FIG. 2 and the sensor tape of FIG. 6.
Figure 7B:
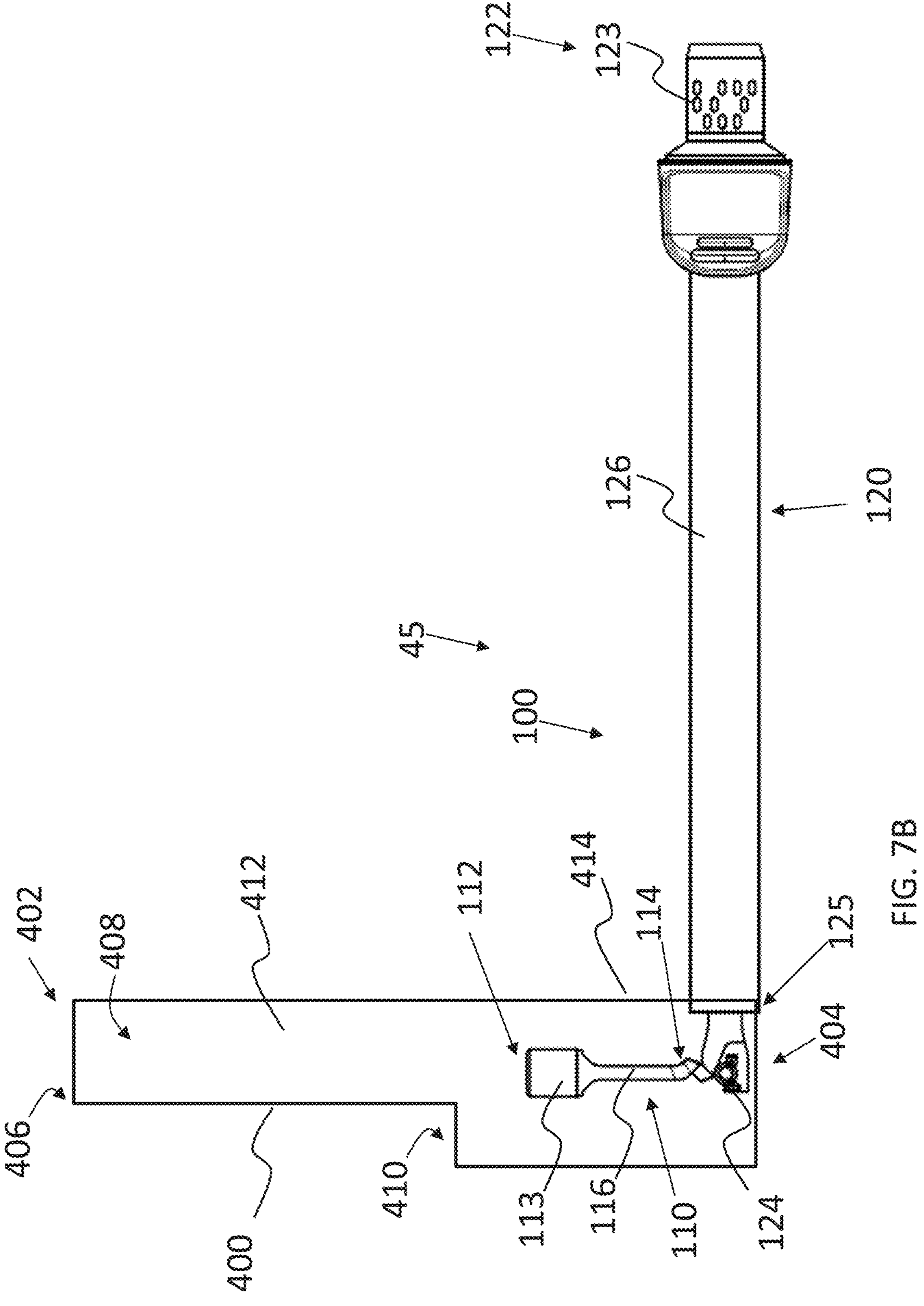
FIG. 7B illustrates a top view of an embodiment of a sensor assembly including the L-shaped sensor of FIG. 2 and the sensor tape of FIG. 6.

FIGS. 7A-B illustrate embodiments of sensor assembly 40, 45 including the L-shaped sensor 100 and the stepped sensor tape 400. As shown in FIGS. 7A-B, the second end 404 of the sensor tape 400 can be proximate the emitter 124. The sensor tap 400 can extend along a length of the detector arm 110, past the detector 113, and terminate at the first end 402. The sensor tape 400 can be substantially parallel to the detector arm 110. The second width and a length of the sensor tape 400 can be sufficient to cover the detector arm 110. In FIG. 7A, the step-like transition 410 of the sensor tape 400 can be closer to the connector arm 120 than the opposite side without the step-like transition. In FIG. 7B, the step-like transition 410 can be further away from the connector arm 120 than the opposite side without the step-like transition. During use, the sensor tape 400 can then be wrapped around the patient's anatomy from the second end 404 to the first end 402. An initial length of the adhesive side 406 of the sensor tape 400, which can include the second portion 414, can directly contact the patient's skin, resulting in a contact area. The contact area between the adhesive side 406 of the sensor tape 400 and the patient's skin is greater than the contact area between the sensor tape 200 and the patient's skin. This is because the sensor tape 400 is wider near the fixed end 114 of the detector arm 110 of the sensor 100 in the sensor assembly 40, 45 than the sensor tape 200 in the sensor assembly 10. The sensor tape 400 in the sensor assembly 40 can advantageously provide greater contact area and thus better securement between the sensor assembly and the patient's skin, thereby minimizing movements of the sensor 100 relative to the patient's skin. Further, after the second portion 414 of the sensor tape 400 has made a first loop around the patient's anatomy, a remaining length of the adhesive side 406 can contact substantially the non-adhesive side 408 of the first loop instead of the patient's skin. The contact between the remaining length of the adhesive side 406 with the non-adhesive side 408 of the first loop can prevent the sensor tape 400 from loosening. Accordingly, the sensor tape 400 of the sensor assembly 40, 45 can provide better securement of the L-shaped sensor 100 by providing a greater contact area between the adhesive side 406 of the sensor tape 400 with the patient skin than the sensor tape 200, but without requiring a significant increase in use of tape materials due to the first portion 412 being narrower than the second portion 414.

Figure 8A:
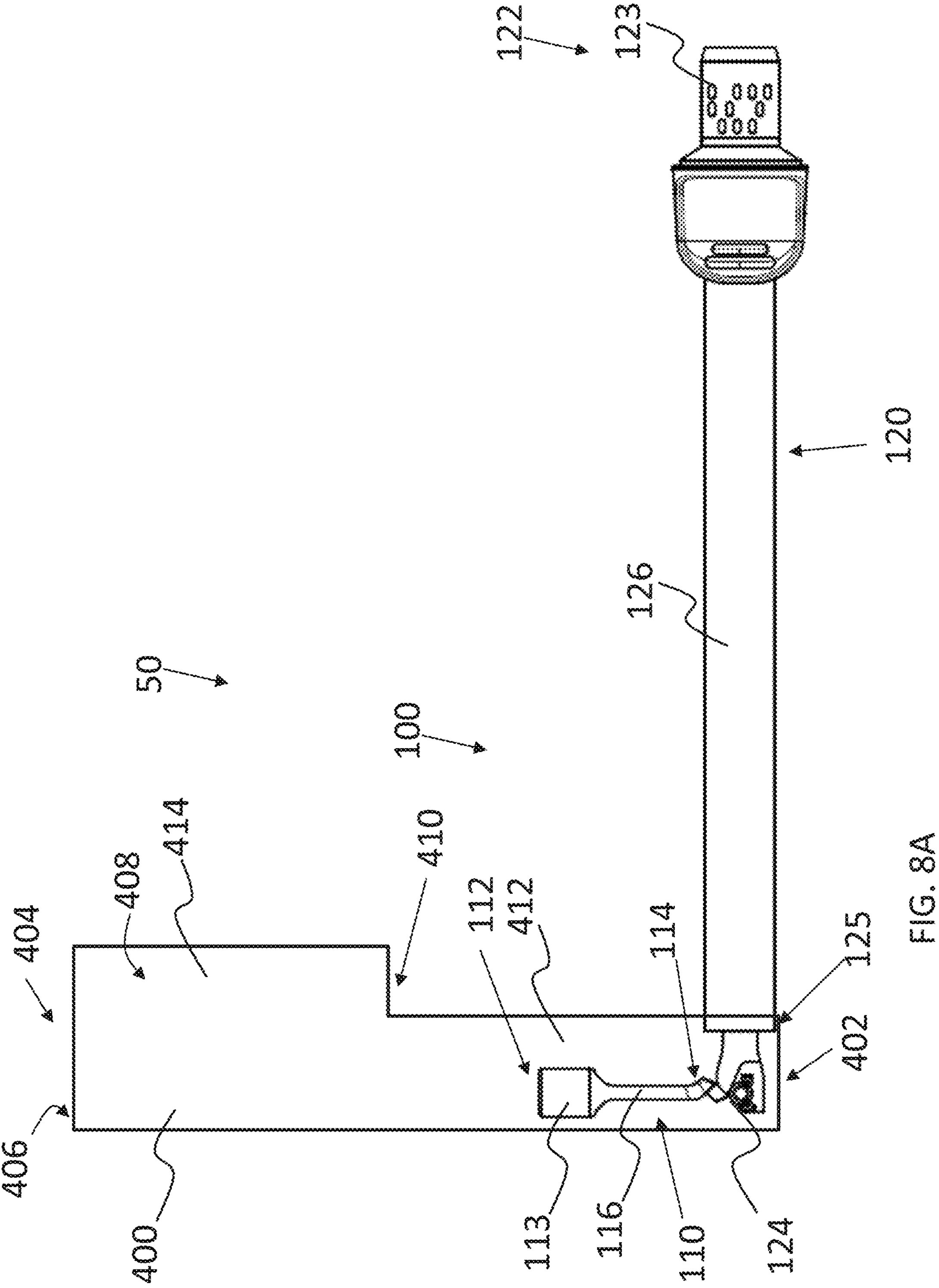
FIG. 8A illustrates a top view of an embodiment of a sensor assembly including the L-shaped sensor of FIG. 2 and the sensor tape of FIG. 6.
Figure 8B:
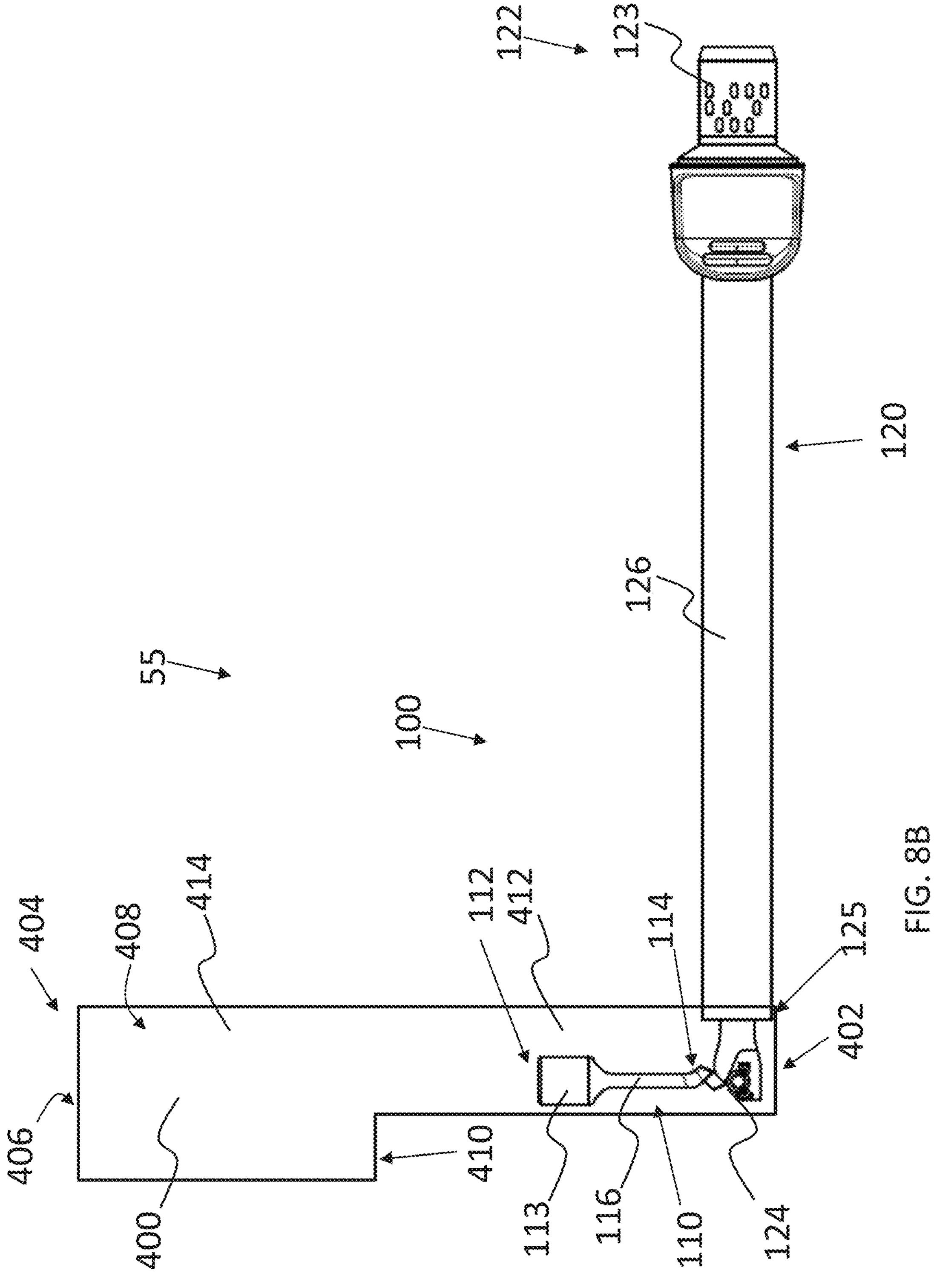
FIG. 8B illustrates a top view of an embodiment of a sensor assembly including the L-shaped sensor of FIG. 2 and the sensor tape of FIG. 6.

FIGS. 8A-B illustrate embodiments of a sensor assembly 50, 55 including the L-shaped sensor 100 and the stepped sensor tape 400. As show in FIGS. 8A-B, the first end 402 of the sensor tape 400 can be proximate the emitter 124. The sensor tape 400 can extend along a length of the detector arm 110, past the detector 113, and terminate at the second end 404. The sensor tape 400 can be substantially parallel to the detector arm 110. The first width of the sensor tape 400 can be sufficient to cover the detector arm 110. In FIG. 8A, the step-like transition 410 of the sensor tape 400 can be closer to the connector arm 120 than the opposite side without the step-like transition. In FIG. 8B, the step-like transition 410 can be further away from the connector arm 120 than the opposite side without the step-like transition. During use, after the narrow first portion 412 of the sensor tape 400 runs out, the adhesive side 406 of the wide second portion 414 can contact partially the non-adhesive side 408 of the narrow first portion 412 and partially the patient's skin not covered by the non-adhesive side 408 of the narrow first portion 412. The total contact area between the sensor tape 400 of the sensor assembly 50, 55 and the patient's skin is higher than the contact area between the sensor tape 200 and the patient's skin. In addition, the narrow first portion 412 can be easier to place on the finger to align the emitter 124 and the detector 113 before the wider second portion 414 can wrap the detector arm 110 and the narrow first portion 412 in place. The wider second portion 414 can attach a portion of the connector arm 120 to the patient's skin. The sensor assembly 50, 55 can therefore better secure the sensor 100 to the patient's skin than the sensor tape 200 and without requiring a significant increase in use of tape materials due to the first portion 412 of the sensor tape 400 of being narrower than the second portion 414.

In some embodiments, the first portion 412 and the second portion 414 of the sensor tape 400 can have substantially equal lengths. In some embodiments, the first portion 412 and the second portion 414 can have different lengths. Ratio of the respective lengths of the first portion 412 and the second portion 414 is not limiting. For example, the first portion 412 can have a length sufficient for making at least one loop around a patient's anatomy. The second portion 414 can have a length sufficient for making at least one loop around a patient's anatomy.

Sloped Sensor Tapes

Figure 9:
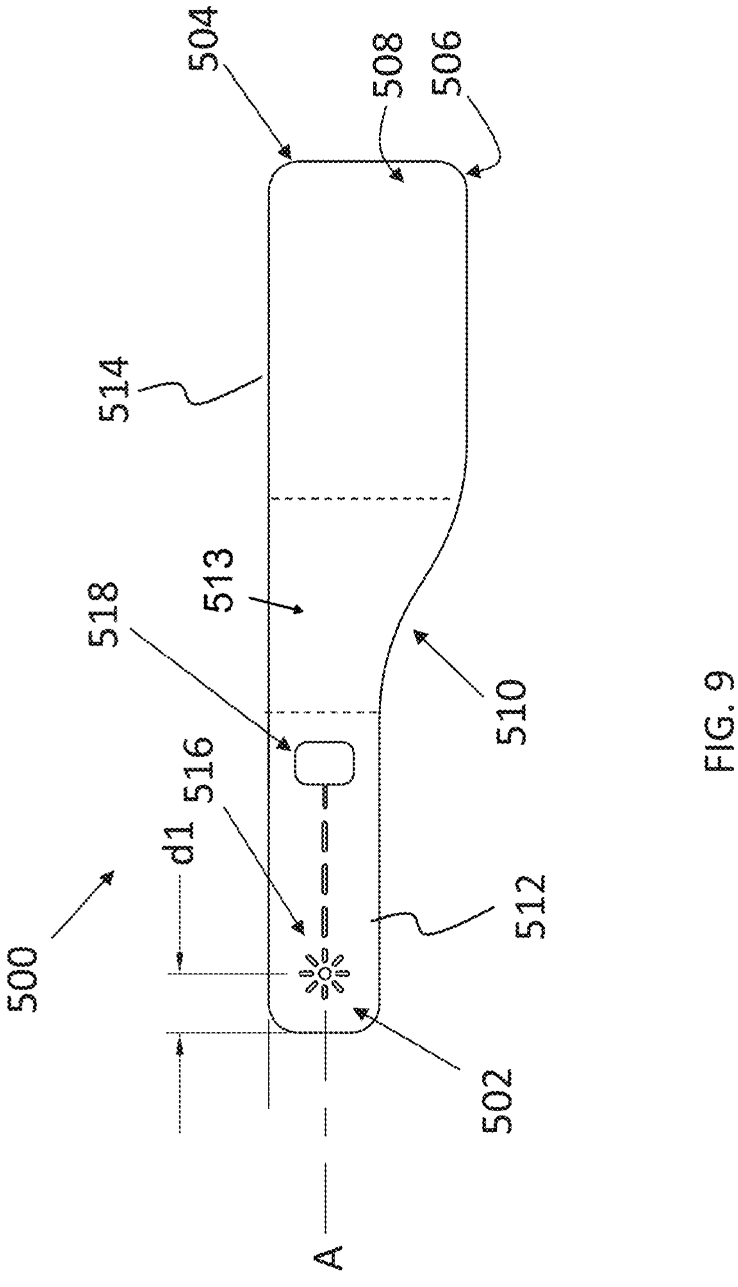
FIG. 9 illustrates a top view of an embodiment of a sensor tape.

FIG. 9 illustrates a top view of a sloped sensor tape 500. The sensor tape 500 can have features of the sensor tapes 200, 300, 400 except as described below. Accordingly, features of the sensor tape 500 can be incorporated into features of the sensor tapes 200, 300, 400 and features of the sensor tapes 200, 300, 400 can be incorporated into features of the sensor tape 500. The sensor tape 500 can have a first end 502 and a second end 504. The sensor tape 500 can have a first width at the first end 502. The sensor tape 500 can have a second width at the second end 504. As show in FIG. 9, the second width is greater than the first width. The first width of the sensor tape 500 can be substantially the same as the first widths of the sensor tapes 200, 300, 400. The sensor tape 500 can transition from the first width to the second width in a slope 510. The slope 510 can be at a location between the first end 502 and the second end 504. The slope 510 can separate the sensor tape 500 into a first portion 512, a second portion 514, and a transition portion 513. The exact geometries of the first portion 512, the second portion 514, and the transition portion 513 are not limiting. For example, at least one of the first portion 512, the second portion 514, and the transition portion can have wavy edges along any sides. The transition portion 513 can have a straight-line slope or a curved slope. The transition portion 513 can have a slope on one side or both sides along the length of the sensor tape 500. The sensor tape 500 can have an adhesive side 506 and a non-adhesive side 508.

With continued reference to FIG. 9, the non-adhesive side 508 of the sensor tape 500 can have alignment indicators 516, 518. The indicator 516 can be aligned with the emitter 124 of the L-shaped sensor 100. The indicator 518 can be aligned with the detector 113 of the L-shaped sensor 100. The alignment indicators 516, 518 can facilitate accurate placement of the detector arm 110 onto the sensor tape 500. For example, both indicators 516, 518 can be centered along a central axis or midline "A" of the narrower first portion 512, as shown in FIG. 9, or along a central axis or midline of the wider second portion 514. A center of the indicator 516 can be a distance d1 from the first end 502 of the sensor tape 500. The alignment indicators 516, 518 can also provide visual aid to a user or a caregiver to ensure that the emitter 124 and the detector 113 are aligned during securement of the sensor 100 to the measurement site with the sensor tape 500.

Figure 10A:
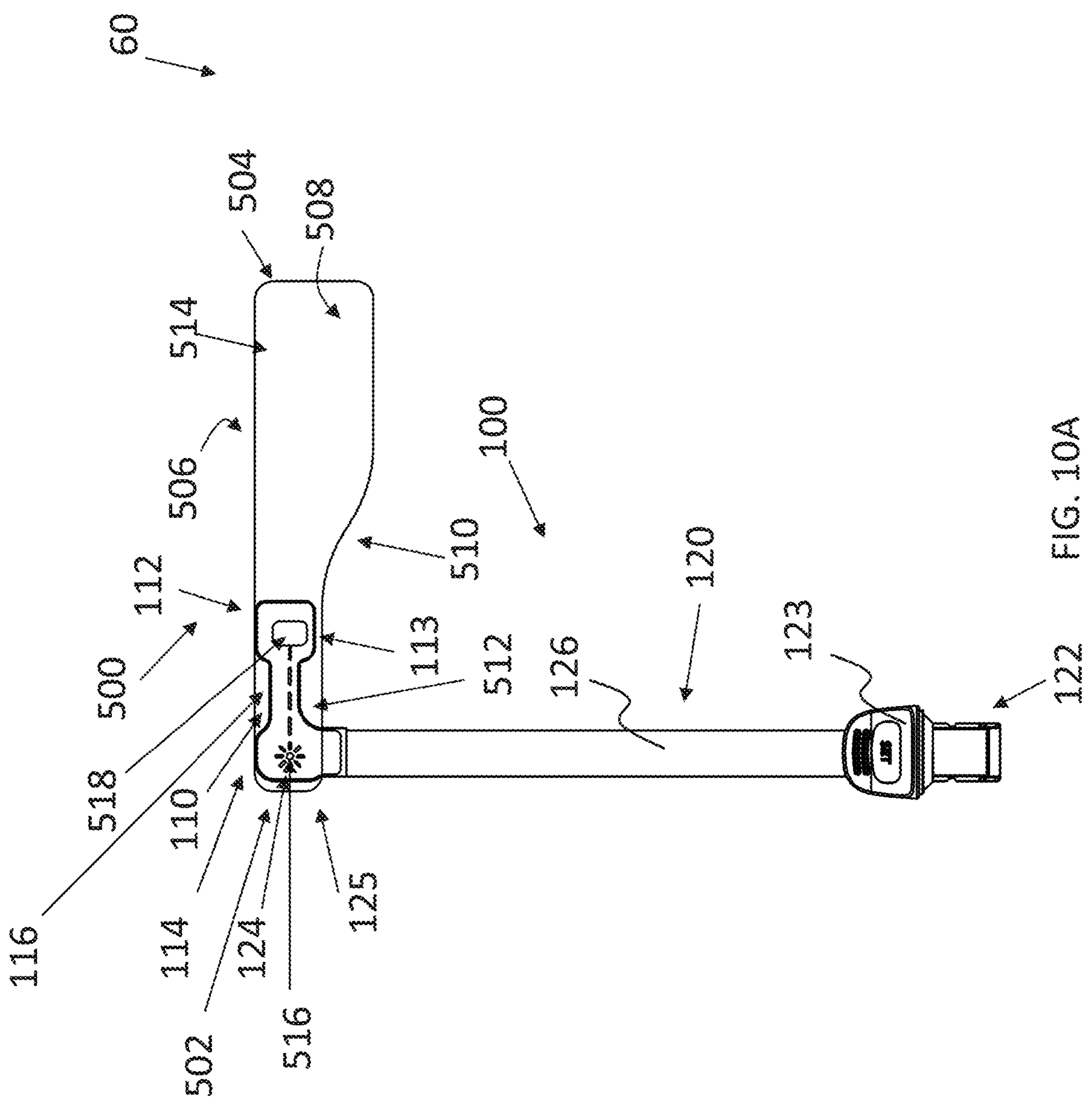
FIGS. 10A-B illustrate top and back perspective views of an embodiment of a sensor assembly including an L-shaped sensor and the sensor tape of FIG. 9.
Figure 10B:
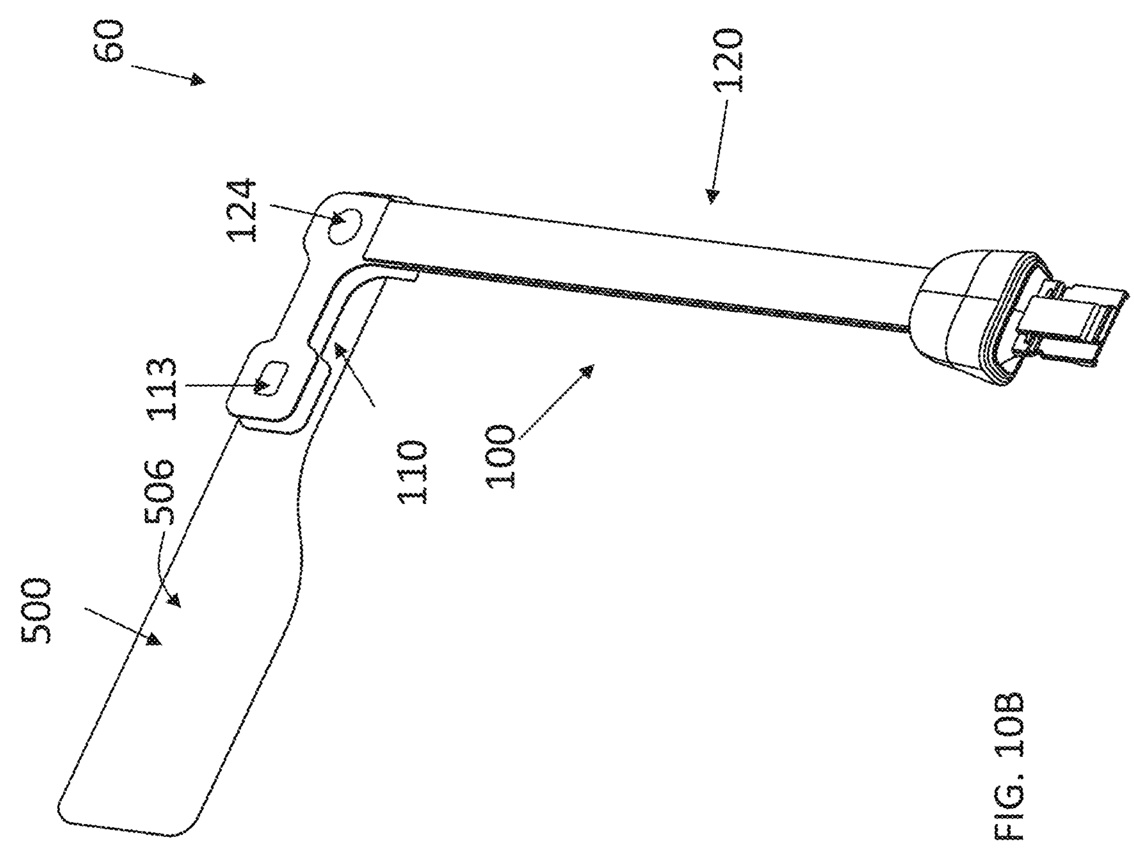
Figure 10C:
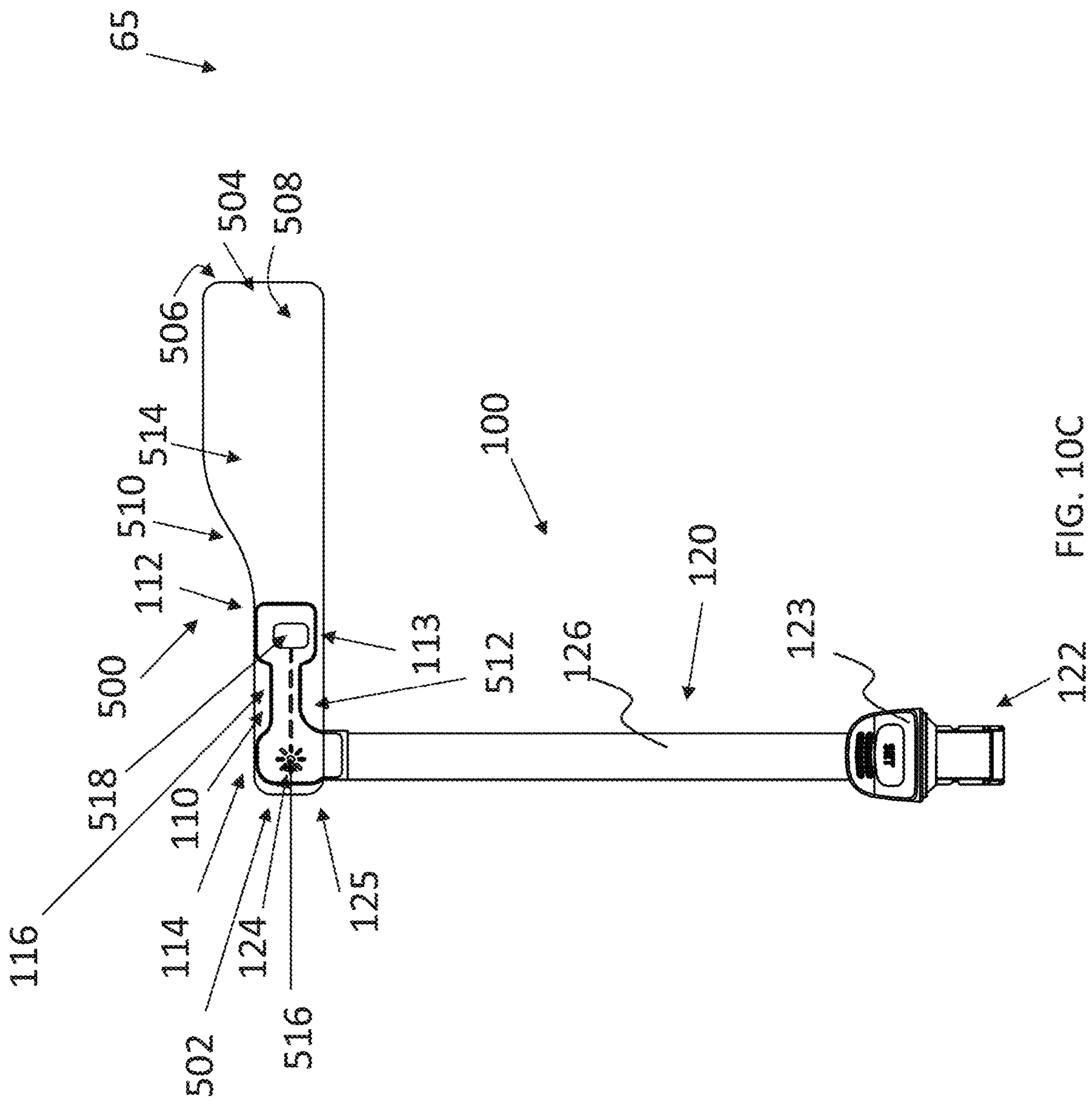
FIG. 10C illustrates a top view of an embodiment of a sensor assembly including an L-shaped sensor and the sensor tape of FIG. 9.
Figure 11A:
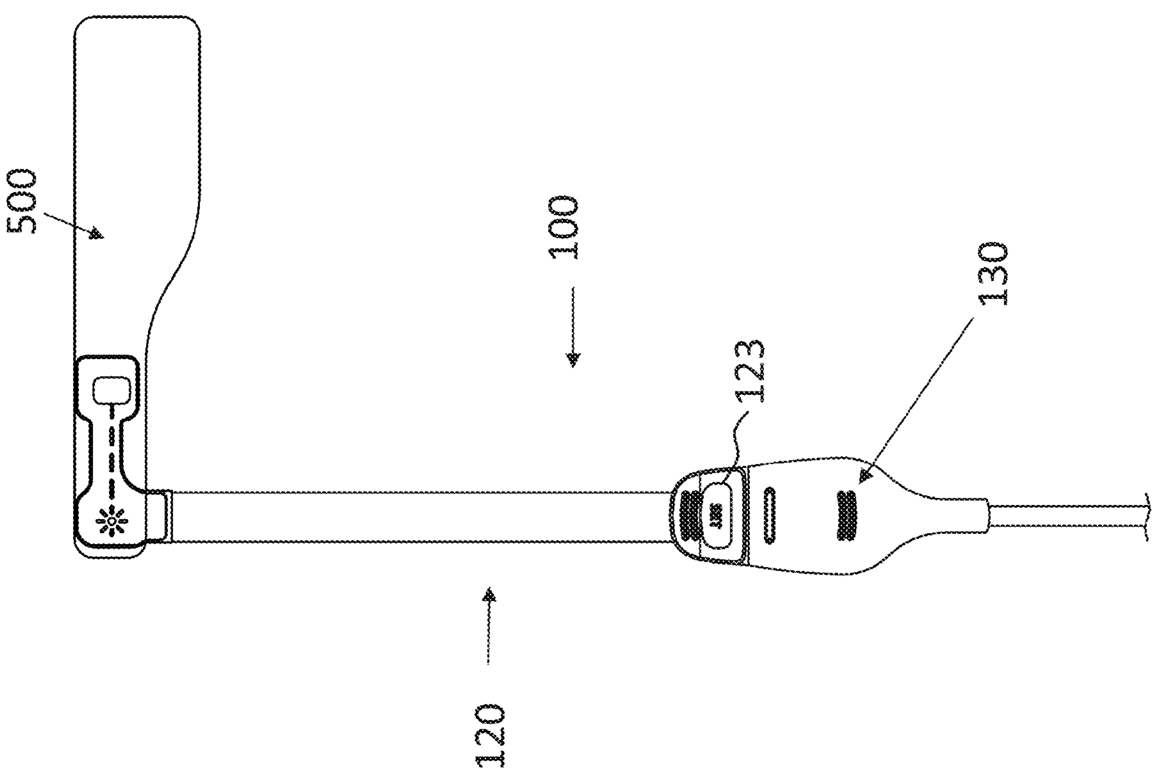
FIGS. 11A-B illustrate top and front perspective views of an embodiment of the sensor assembly of FIGS. 10A-B connected to a sensor cable.
Figure 11B:
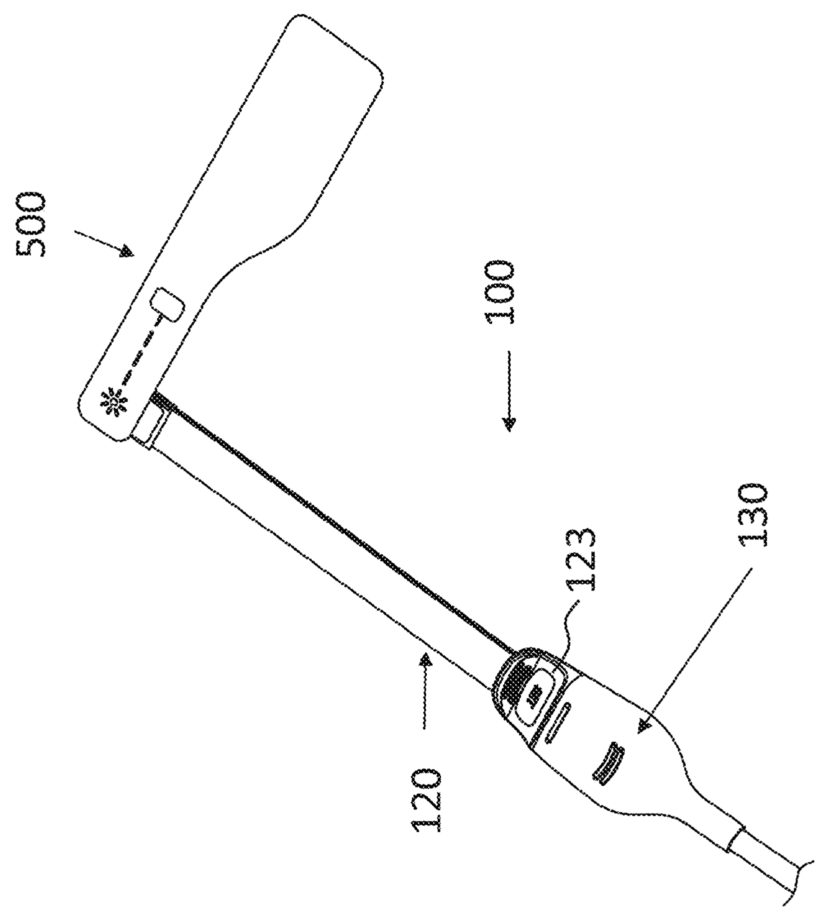

FIGS. 10A-C illustrate embodiments of a sensor assembly 60, 65 including the L-shaped sensor 100 and the sloped sensor tape 500. FIGS. 11A-B illustrate the sensor assembly 60 including the L-shaped sensor 100 and the sloped sensor tape 500 being connected to a sensor cable 130 at the cable connector 123. As shown in FIGS. 10A-C, the first end 502 of the sensor tape 500 can be proximate the emitter 124. The indicator 516 can be aligned with the emitter 124. The sensor tape 500 can be substantially parallel to the detector arm 110. The sensor tape 500 can extend along the length of the detector arm 110, past the detector 113, and terminate at the second end 504. The first width and a length of the sensor tape 400 can be sufficient to cover the detector arm 110. The indicator 518 can be aligned with the detector 113. In FIGS. 10A-B, the slope 510 of the sensor tape 500 can be closer to the connector arm 120 than the opposite side without the slope. In FIG. 10C, the slope 510 can be further away from the connector arm 120 than the opposite side without the slope. During use, the narrow first portion 512 of the sensor tape 500 can contact the patient's skin at or near the measurement site. As shown in FIGS. 10A-C, the narrow first portion 512 terminates at or near the free end 112 of the detector arm 110. The first portion 512 can cover approximately half a loop around the patient's anatomy. The adhesive side 506 of the increasingly wider transition portion 513 can contact the patient's skin along a portion of or an entire second half of the loop around the patient's anatomy. After the transition portion 513 runs out, the adhesive side 506 of the wider second portion 514 can contact partially the non-adhesive side 508 of the narrow first portion 512 and/or the transition portion 513, and partially the patient's skin not covered by the non-adhesive side 508 of the first portion 512 and/or the transition portion 513. The total contact area between the sensor tape 500 of the sensor assembly 60 and the patient's skin is higher than the contact area between the sensor tape 200 and the patient's skin. In addition, the narrow first portion 512 can be easier to place on the finger to align the emitter 124 and the detector 113 before the wider second portion 514 can wrap the detector arm 110 and the narrow first portion 512 in place. The transition portion 513 and the wider second portion 514 can attach a portion of the connector arm 120 to the patient's skin. The sensor assembly 60 can therefore better secure the sensor 100 to the patient's skin than the sensor tape 200 and without requiring a significant increase in use of tape materials due to the first portion 512 and the transition portion 513 of the sensor tape 500 being narrower than the second portion 514.

The transition portion 513 of the sloped sensor tape 500 can avoid sharp corners of a stepped transition. The transition portion 513 can thus reduce tearing of a sensor tape at or around the sharp corner when applying or removing the sensor tape. As show in FIG. 10B, the detector arm 110 of the sensor 110 is placed beneath or immediately next to the adhesive side 506 of the sensor tape 500. The emitter 124 and the detector 113 can be aligned to the indicators 516, 518 as discussed above to ensure that the detector arm 110 is placed within the boundary of the sensor tape 500. Placing the sensor 100 next to the adhesive side 506 of the sensor tape 500 can allow the sensor and the tape be assembled right before use. The sensor tape 500 can come in a variety of sizes, such as small, medium, and large. The appropriately sized sensor tape 500 can be selected depending on the size of the patient's anatomy. The separability of the sensor tape 500 from the sensor 100 can allow the sensor tape 500 to be disposable so that a new sensor tape 500 with a fresh adhesive side 506 can be used for every measurement site to improve securement of the sensor 100 to the measurement site. The separability of the sensor tape 500 from the sensor 100 can allow the more expensive components, such as the emitter 124, the detector 113, and other electrical components, be reusable. Reusing the more expensive components can reduce cost of replacing the optical sensors.

Similar to the assemblies of the sensor tapes 300, 400 and the L-shaped sensor 100 described above, the sensor tape 500 can be used with the sensor 100 such that the second side 504 is approximate the emitter 124. The indicators can be placed on the second portion 514 and be centered on the central axis or midline of the wider second portion 514.

Staggered Sensor Tapes

Figure 12:
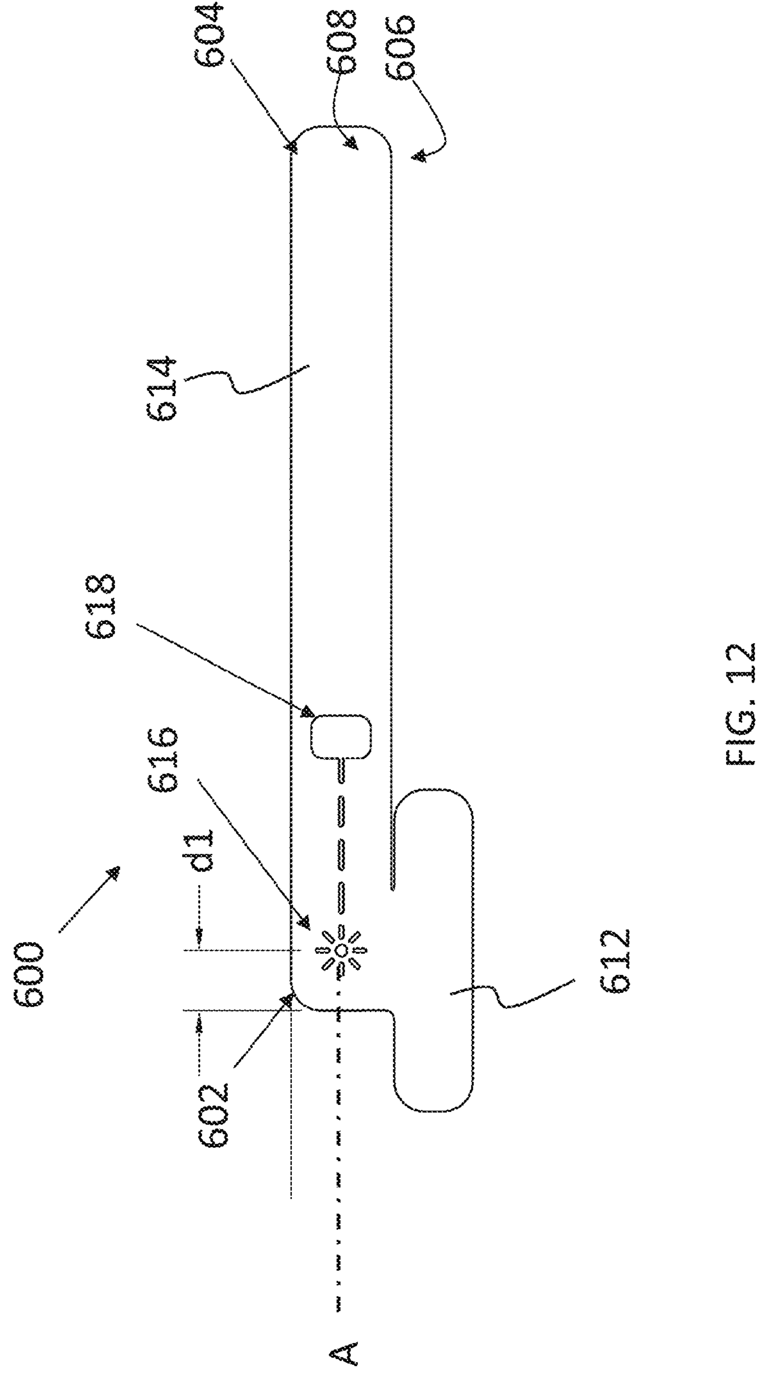
FIG. 12 illustrates a top view of an embodiment of a sensor tape.

FIG. 12 illustrates a top view of a staggered sensor tape 600. The sensor tape 600 can have features of the sensor tapes 200, 300, 400, 500 except as described below. Accordingly, features of the sensor tape 600 can be incorporated into features of the sensor tapes 200, 300, 400, 500 and features of the sensor tapes 200, 300, 400, 500 can be incorporated into features of the sensor tape 600. The sensor tape 600 can have a first portion 612 and a second portion 614. The first and second portions 612, 614 can be cut from the same piece of tape material. The first and second portions 612, 614 can be an integral sensor tape. The first and second portions 612, 614 can be connected at a first end 602 of the second portion 614 such that sections of the two portions are staggered. The first portion 612 can be substantially centered at the first end 602 of the second portion 614 such that one end of the first portion 612 extends beyond the first end 602 of the second portion 614. In other embodiments, the first portion 612 can have about ⅔ of its length extending beyond the first end 602 of the second portion 614 and the remaining about ⅓ of its length aligned with the second portion 614. The length of the first portion 612 that extends beyond the first end 602 of the second portion 614 is not limiting. The first portion 612 can have a first width. The second portion 614 can have a second width. The second portion 614 can have a second end 604 opposite the first end 602 along a length of the second portion 614. The length of the second portion 614 can be greater than a length of the first portion 612. As show in FIG. 12, the second width is greater than the first width. The first and second widths can be substantially the same. The second width can be smaller than the first width. The second width of the sensor tape 600 can be substantially the same as the first widths of the sensor tapes 200, 300, 400, 500. The exact geometries of the first portion 612 and the second portion 614 are not limiting. For example, at least one of the first portion 512 and the second portion 614 can have straight or wavy edges along any sides.

With continued reference to FIG. 12, the sensor tape 600 can have an adhesive side 606 and a non-adhesive side 608. The non-adhesive side 608 of the sensor tape 600 can have alignment indicators 616, 618. The indicator 616 can be aligned with the emitter 124 of the L-shaped sensor 100. The indicator 618 can be aligned with the detector 113 of the L-shaped sensor 100. The alignment indicators 616, 618 can facilitate accurate placement of the detector arm 110 onto the sensor tape 600. For example, both indicators 616, 618 can be centered along a central axis or midline "A" of the wider second portion 614, as shown in FIG. 12, or along a central axis or midline of the narrow first portion 612. A center of the indicator 616 can be a distance d1 from the first end 602 of the sensor tape 600. The alignment indicators 616, 618 can also provide visual aid to a user or a caregiver to ensure that the emitter 124 and the detector 113 are aligned during securement of the sensor 100 to the measurement site with the sensor tape 600.

Figure 13A:
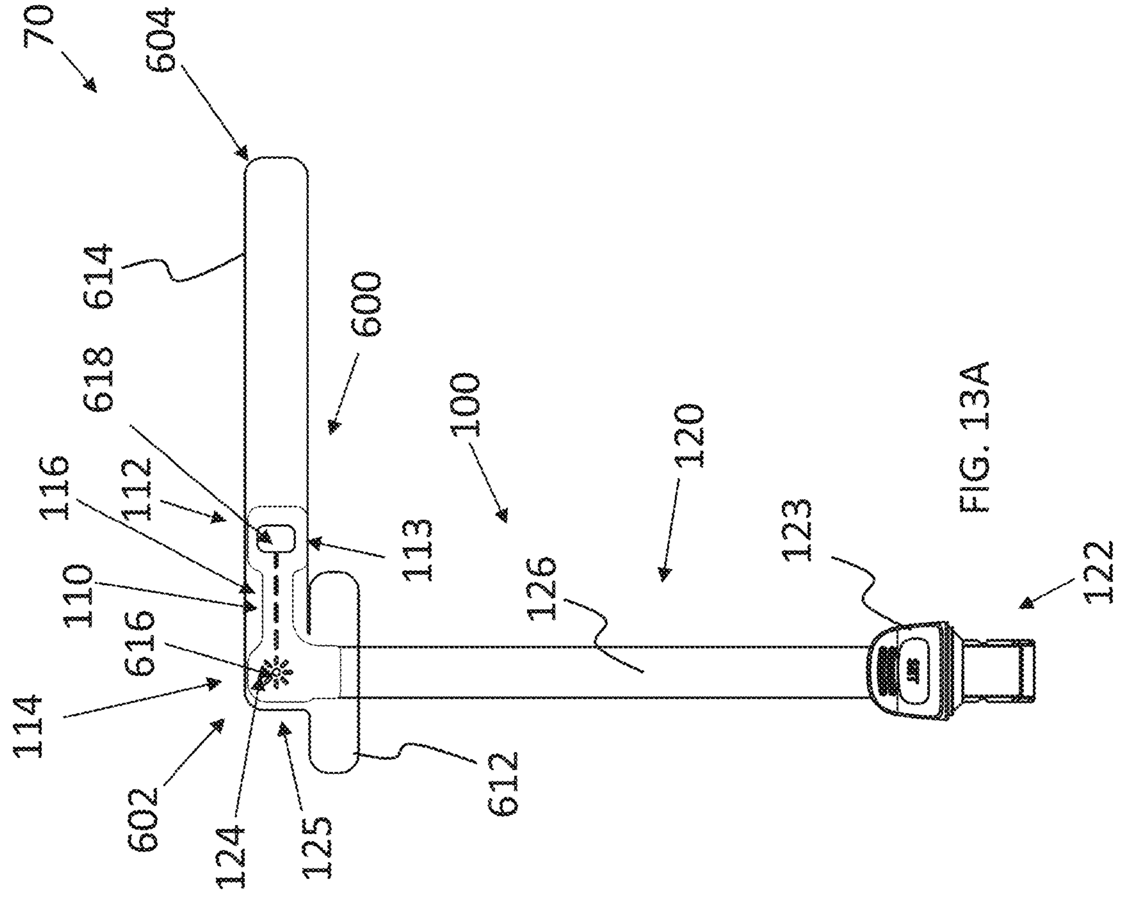
FIGS. 13A-B illustrate top and back perspective views of an embodiment of a sensor assembly including an L-shaped sensor and the sensor tape of FIG. 12.
Figure 13B:
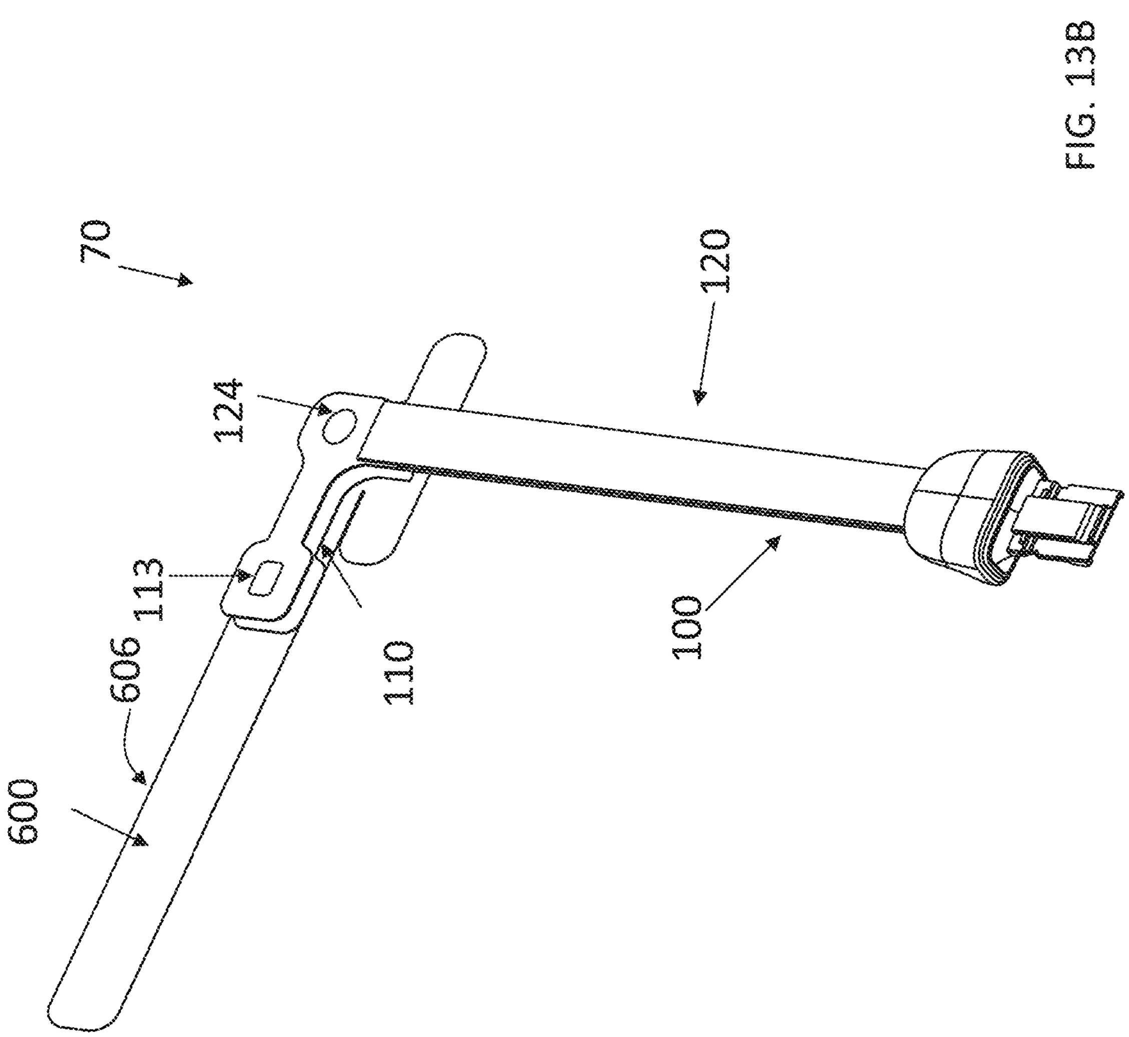
Figure 13C:
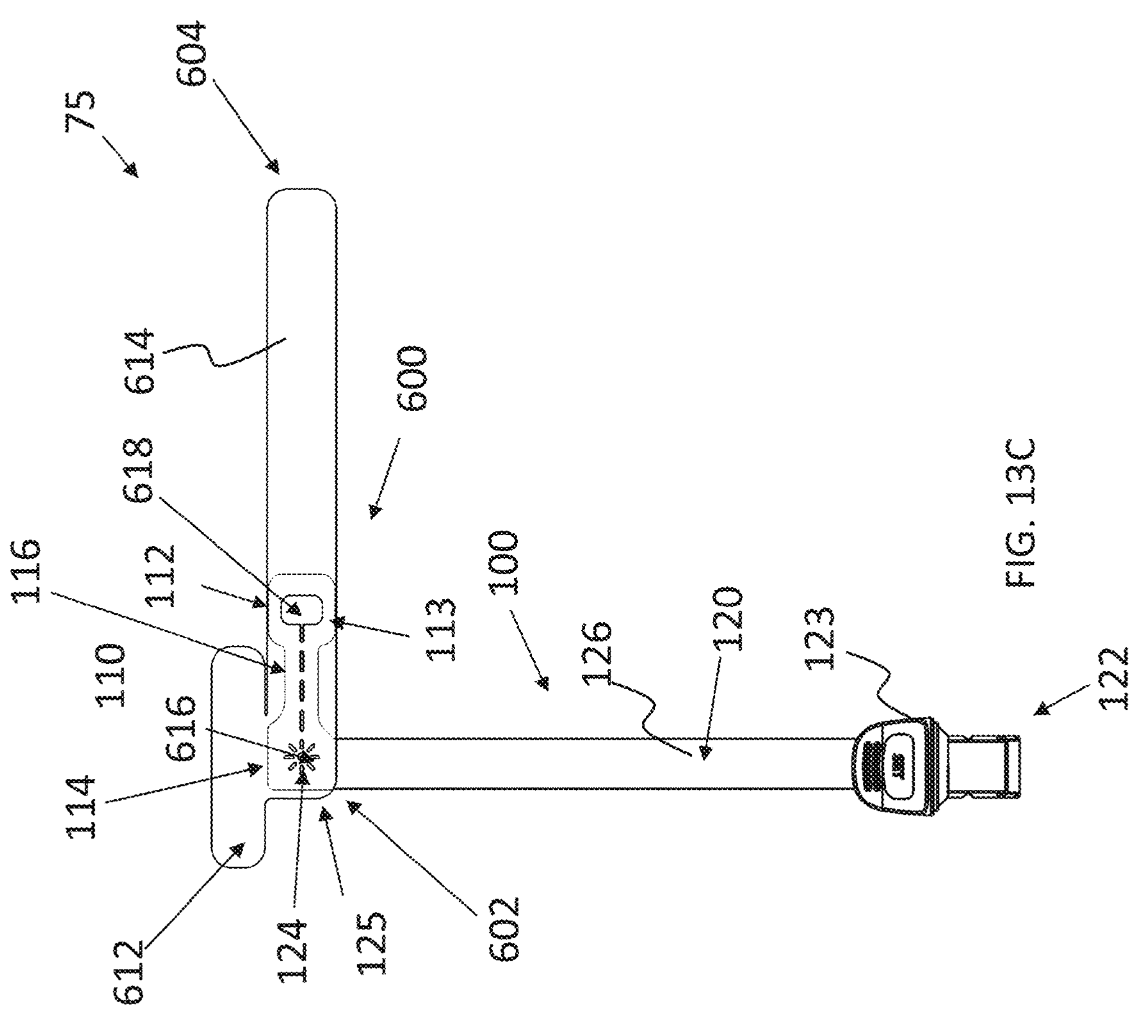
FIG. 13C illustrates a top view of an embodiment of a sensor assembly including an L-shaped sensor and the sensor tape of FIG. 12.
Figure 14A:
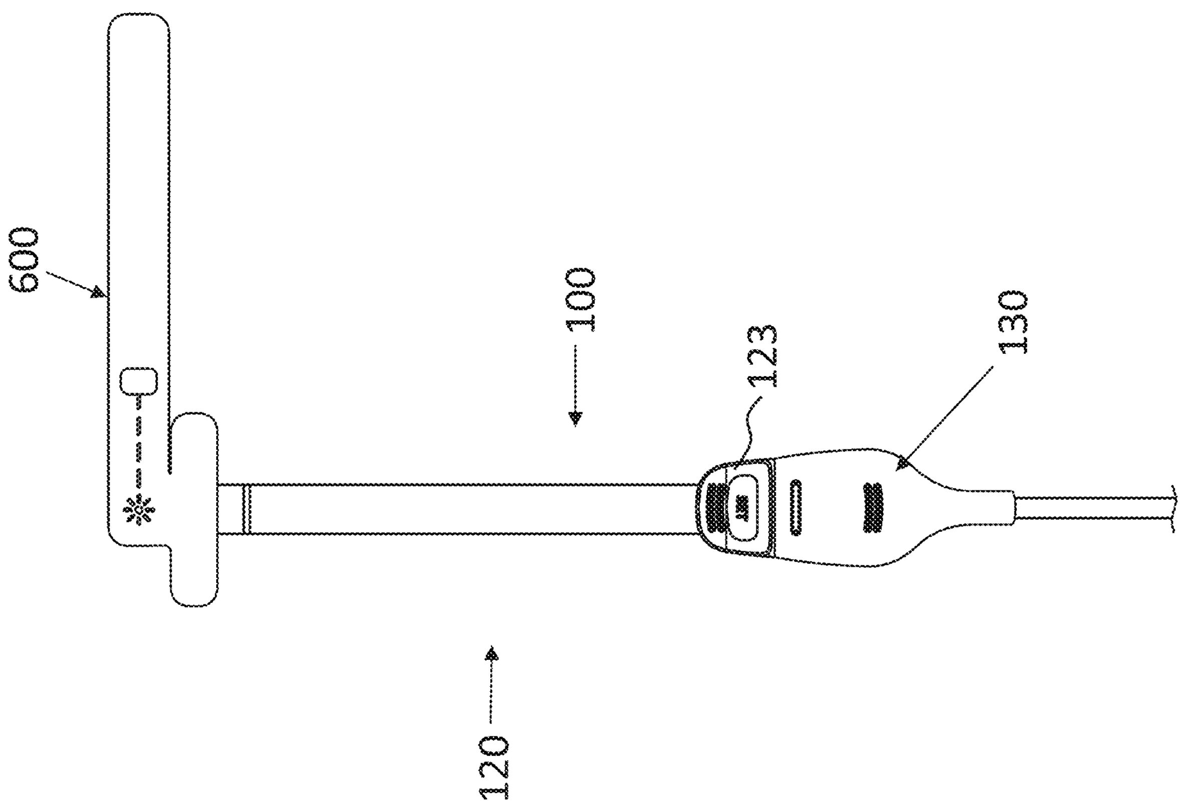
FIGS. 14A-B illustrate top and front perspective views of an embodiment of the sensor assembly of FIGS. 13A-B connected to a sensor cable.
Figure 14B:
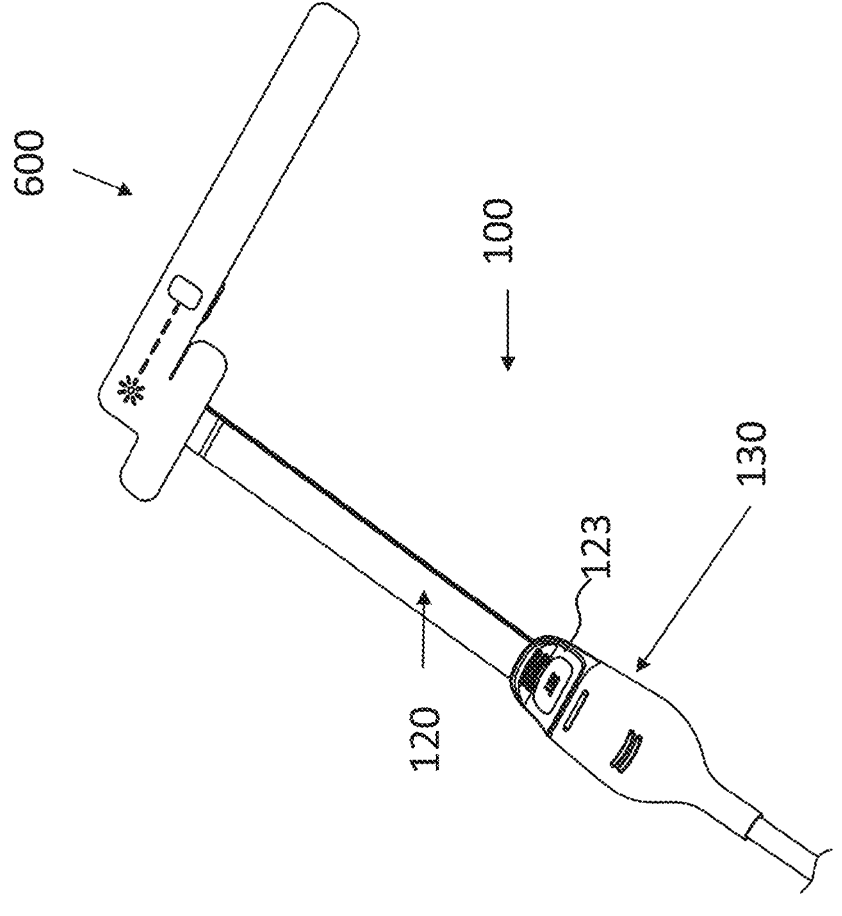

FIGS. 13A-C illustrate embodiments of a sensor assembly 70, 75 including the L-shaped sensor 100 and the staggered sensor tape 600. FIGS. 14A-B illustrate the sensor assembly 70 including the L-shaped sensor 100 and the staggered sensor tape 600 being connected to a sensor cable 130 at the cable connector 123. As shown in FIGS. 13A-C, the first end 602 of the sensor tape 600 can be proximate the emitter 124. The indicator 616 can be aligned with the emitter 124. The sensor tape 600 can extend along the length of the detector arm 110, past the detector 113, and terminate at the second end 604. The sensor tape 600 can be substantially parallel to the detector arm 110. The second width of the sensor tape 600 can be sufficient to cover the detector arm 110. The indicator 618 can be aligned with the detector 113. In FIGS. 13A-B, the first portion 612 of the sensor tape 500 can be closer to the connector arm 120 than the second portion 614. In FIG. 13C, the first portion 612 can be further away from the connector arm 120 than the second portion 614. During use, the wider second portion 614 and the narrow first portion 612 of the sensor tape 600 can each contact the patient's skin at or near the measurement site. The wider second portion 614 and the narrow first portion 612 of the sensor tape 600 can form independent, staggered loops around the patient's anatomy. In addition, the total contact area between the sensor tape 600 of the sensor assembly 70, 75 and the patient's skin is higher than the contact area between the sensor tape 200 and the patient's skin. The sensor assembly 70, 75 can therefore better secure the sensor 100 to the patient's skin than the sensor tape 200 and without requiring a significant increase in use of tape materials due to the first portion 612 of the sensor tape 600 being narrower and/or shorter than the second portion 614. Further, the first portion 612 of the sensor assembly 70 can attach a portion of the connector arm 120 to the patient's skin.

The staggered first and second portion 612, 614 can each form at least a first loop around the patient's anatomy without layer(s) of tape between the first or second portions 612, 614 and the patient's skin. The staggered first and second portion 612, 614 can thus result in even tape surfaces around the patient's anatomy. An even tape surface can provide better securement of the tape to the skin because there is no gap that could sometimes form when the adhesive side of a tape is placed partially over the skin and partially over a non-adhesive side of the previous loop of tape. The staggered first and second portion 612, 614 can also provide a mechanical decoupling along a joint of an appendage, such as a finger. The first and second portions 612, 614 can be placed above and below a joint respectively. The first and second portions 612, 614 can stay securely connected to the patient skin despite small movements of the patient, such as flexing of a finger or a foot, because the first and second portions 612, 614 are not connected along an entire length of the staggered sections. This can allow the finger to bend freely, but still maintain the tape in substantially the same position due to the increased adhesive surface provided by the first portion 612. As show in FIG. 14B, the detector arm 110 of the sensor 110 is placed beneath or immediately next to the adhesive side 606 of the sensor tape 600. The emitter 124 and the detector 113 can be aligned to the indicators 616, 618 respectively as discussed above to ensure that the detector arm 110 is placed within the boundary of the sensor tape 600. Placing the sensor 100 next to the adhesive side 606 of the sensor tape 600 can allow the sensor 100 and the tape 600 be assembled right before use. The sensor tape 600 can come in a variety of sizes, such as small, medium, and large. The appropriately sized sensor tape 600 can be selected depending on the size of the patient's anatomy. The separability of the sensor tape 600 from the sensor 100 can allow the sensor tape 600 be disposable so that a new sensor tape with a fresh adhesive side can be used for every measurement site to improve securement of the sensor to the measurement site. The separability of the sensor tape 600 from the sensor 100 can allow the more expensive components, such as the emitter 124, the detector 113, and other electrical components be reusable. Reusing the more expensive components can reduce cost of replacing the optical sensors.

Figure 15:
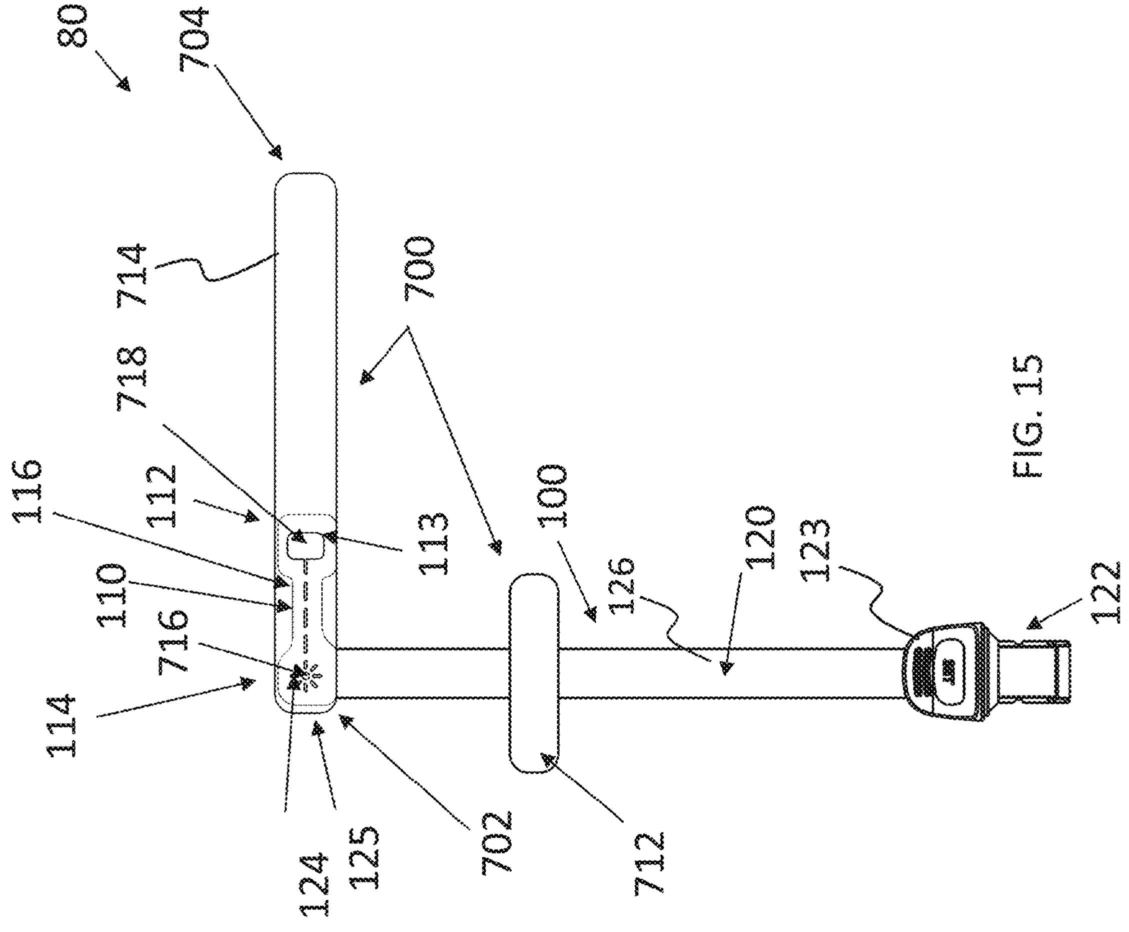
FIG. 15 illustrates a top view of an embodiment of a sensor assembly including an L-shaped sensor and a two-piece staggered sensor tape.

FIG. 15 illustrates a top view of a sensor assembly 80 including the L-shaped sensor 100 and a staggered sensor tape 700. The sensor tape 700 can have features of the sensor tapes 200, 300, 400, 500, 600 except as described below. Accordingly, features of the sensor tape 700 can be incorporated into features of the sensor tapes 200, 300, 400, 500, 600 and features of the sensor tapes 200, 300, 400, 500, 600 can be incorporated into features of the sensor tape 700. The sensor tape 700 can have a first portion 712 and a second portion 714. The first and second portions 712, 714 of the sensor tape 700 can each have an adhesive side and a non-adhesive side. The non-adhesive side of the second portion can include alignment indicators 716, 718. The second portion 714 can have a first end 702 and a second end 704 opposite the first end 702 along a length of the second portion 714. The first end 702 of the second portion 714 can be proximate the emitter 124. The indicator 716 can be aligned with the emitter 124. The sensor tape 700 can extend along the length of the detector arm 110, past the detector 113, and terminate at the second end 604. The sensor tape 700 can be substantially parallel to the detector arm 110. The indicator 718 can be aligned with the detector 113 of the L-shaped sensor 100. The alignment indicators 716, 718 can have the advantages described above. The first portion 712 can be detached from the second portion 714. The first portion 712 can be placed closer to the cable connector 123 than the second portion 714. The first portion 712 can be generally centered at the connector arm 120. A mid-point of the first portion 712 along a length of the first portion 712 can be offset from a midline along a length of the connector arm 120. The offset can be on the same side of the connector arm 120 as the detector 110 or on the opposite side. The first portion 712 can stabilize a portion of the connector arm 120 to the patient's skin, thereby facilitating the secure attachment of the sensor assembly 80 with the measurement site.

Manufacturing of Sensor Tapes

Figures 16A, 16B:
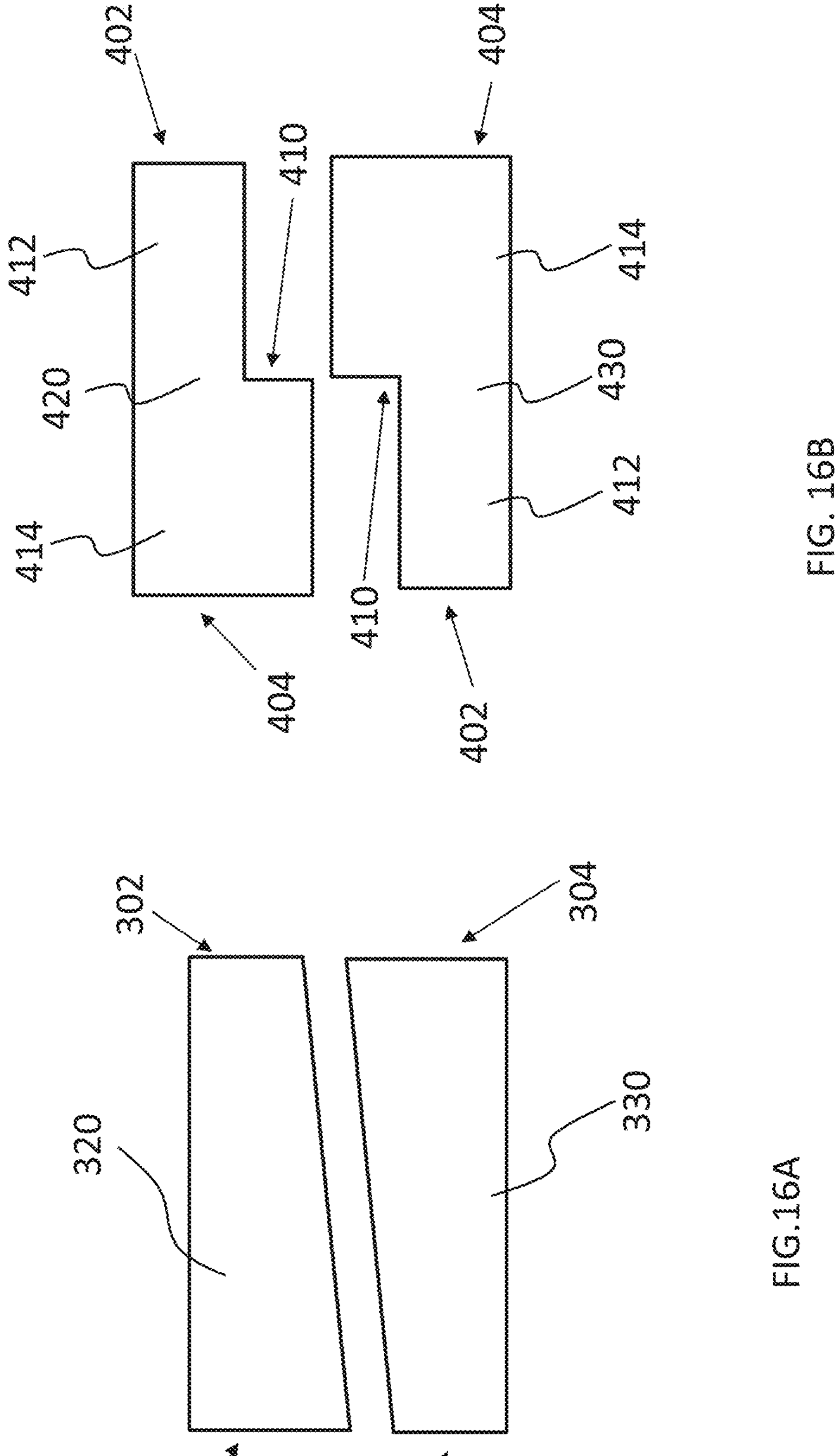
FIGS. 16A-C illustrate methods of manufacturing the sensor tapes of FIGS. 3, 6, and 9.
Figure 16C:
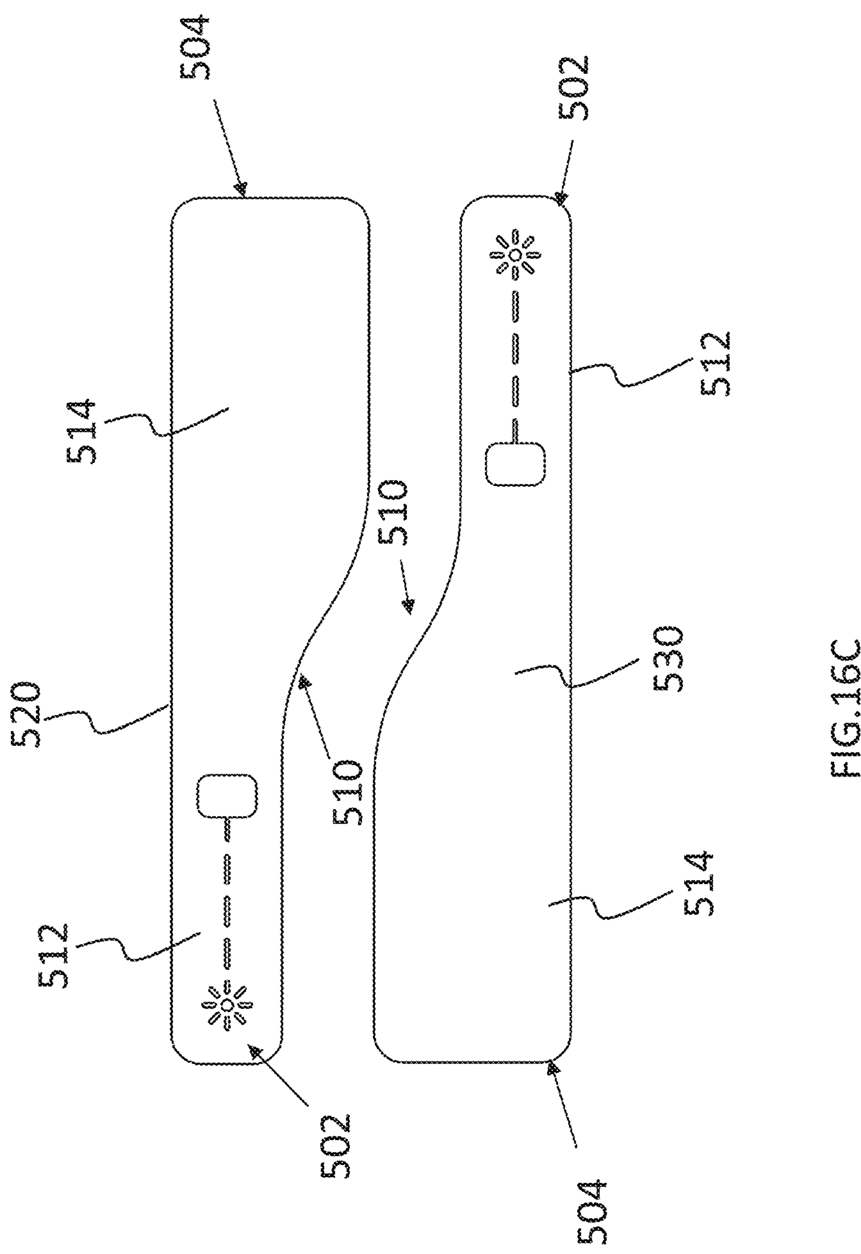

Certain manufacturing techniques for saving materials will now be described with reference to FIGS. 16A-C. As shown in FIG. 16A, during manufacturing, a top sensor tape 320 and a bottom sensor tape 330 can be cut from a rectangular piece of sensor tape material by a diagonal cut. The first and second ends of the bottom sensor tape 330 can be flipped horizontally in the cut pattern so that the first end 302 of the top sensor tape 320 aligns with the second end 304 of the bottom sensor tape 330 and the second end 304 of the top sensor tape 320 aligns with the first end 302 of the bottom sensor tape 330. As shown in FIG. 16B, during manufacturing, two pieces of the sensor tape 420, 430, each with the first and second portions 412, 414, can be cut from a rectangular piece of sensor tape material by a zig-zag lined cut. This manufacturing technique is especially advantageous if the first and second portions 412, 414 have the same length. The first and second ends of the bottom sensor tape 430 can be flipped in the cut pattern so that the first portion 412 of the top sensor tape 420 aligns with the second portion

414 of the bottom sensor tape 430 and the second portion 414 of the top sensor tape 420 aligns with the first portion 412 of the bottom sensor tape 430. Likewise, as shown in FIG. 16C, during manufacturing, two pieces of the sensor tape 520, 530 can be cut from a rectangular piece of sensor tape material by a zig-zag lined cut, especially if the first and second portions 512, 514 have the same length. The first and second ends of the bottom sensor tape 530 can be flipped in the cut pattern so that the first portion 512 of the top sensor tape 520 aligns with the second portion 514 of the bottom sensor tape 530 and the second portion 514 of the top sensor tape 520 aligns with the first portion 512 of the bottom sensor tape 530. As shown, the sensor tapes 300, 400, 500 can be manufactured with less waste in tape material despite the non-uniform widths of the tapes.

In some embodiments, the sensor assembly 10, 20, 25, 30, 35, 40, 45, 50, 55, 60, 65, 70, 75, 80 can have two layers of sensor tapes instead of only one layer of sensor tape 200, 300, 400, 500, 600, 700. The detector arm 100 can be sandwiched between the two layers of sensor tapes. The tape layer interfacing the detector arm 100 and the patient's skin can have two adhesive sides. The two layers of sensor tapes can have the same or different shapes and/or sizes.

In some embodiments, the sensor assembly 10, 20, 25, 30, 35, 40, 45, 50, 55, 60, 65, 70, 75, 80 can optionally include a liner and applicator tape (not shown). The liner can be printed with a variety of designs and/or colors. The liner can be long and wide enough to fit the length of the sensor tape 200, 300, 400, 500, 600, 700. The applicator tape can have a variety of shapes and sizes. In one embodiment, the applicator tape has a length and width that can fit onto the liner. Additional details regarding the liner and applicator tape and other features can be found in U.S. application Ser. No. 15/017,505, reference herein.

In some embodiments, the sensor tape 200, 300, 400, 500, 600, 700 can be used to secure any types of sensor to a patient's skin to form a sensor assembly. In some embodiments, the sensor tape 200, 300, 400, 500, 600, 700 can be used to secure any types of sensor to a surface of a medium other than a patient's skin to taking non-invasive measurement of characteristics of a medium.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive L-shaped sensor configured to be applied to a skin surface of a neonatal or infant patient for measuring physiological parameters of the neonatal or infant patient, the noninvasive L-shaped sensor comprising:

a flat detector strip comprising an optical emitter and an optical detector spaced along a longitudinal axis of the detector strip, the detector strip having a length along the longitudinal axis between a first end and a second end of the detector strip, wherein the detector strip is configured to be wrapped onto a body part of the neonatal or infant patient; and a flat connector strip perpendicular to the longitudinal axis of the detector strip such that the connector strip extends away from the detector strip, a first end of the connector strip lengthwise being connected to the detector strip, the first end of the connector strip being aligned with the optical emitter, a second end of the connector strip opposite the first end of the connector strip terminating at a cable connector, an electrical circuit extending between the first and second ends of the connector strip, the electrical circuit electrically connecting the optical emitter, the optical detector, and the cable connector, wherein the cable connector is configured to be plugged into a corresponding port of a sensor cable, and wherein the connector strip comprises a flexible flat foam configured to protect the electrical circuit along the connector strip and extending between the cable connector and the optical emitter, the connector strip defining first and second opposing substantially planar faces extending from the first end to the second end of the connector strip, and wherein the electrical circuit is carried along the flat connector strip between the first and second ends without protruding beyond either of the opposing substantially planar faces.

2. The noninvasive L-shaped sensor of claim 1, wherein the optical emitter is closer to the first end of the flat detector strip than the optical detector.

3. The noninvasive L-shaped sensor of claim 2, wherein, when in use, an initial portion of the flat detector strip starting from the first end of the detector strip and encompassing the optical emitter and the optical detector is configured to directly contact the skin surface.

4. The noninvasive L-shaped sensor of claim 3, wherein a terminal portion of the flat detector strip ending at the second end of the detector strip is configured to contact the initial portion.

5. The noninvasive L-shaped sensor of claim 1, wherein the length of the flat detector strip is at least twice of a distance between the optical emitter and the optical detector so as to wrap around the body part in more than one loop.

6. The noninvasive L-shaped sensor of claim 5, wherein the distance between the optical emitter and the optical detector is such that, when wrapped onto the body part of the neonatal or infant patient, the optical emitter and the optical detector are on opposite sides of the body part.

7. The noninvasive L-shaped sensor of claim 1, wherein the flat detector strip comprises a first surface and a second surface opposite the first surface, the first surface configured to face the skin surface and the second surface configured to face away from the skin surface.

8. The noninvasive L-shaped sensor of claim 7, wherein the second surface of the flat detector strip comprises a first alignment indicator aligned with the optical emitter and a second alignment indicator aligned with the optical detector.

9. The noninvasive L-shaped sensor of claim 7, wherein the first surface of the flat detector strip is an adhesive surface.

10. The noninvasive L-shaped sensor of claim 1, wherein the sensor is configured to be removably attached to the body part with hook and loop.

11. The noninvasive L-shaped sensor of claim 1, wherein the flat connector strip is rectangular in shape.

12. The noninvasive L-shaped sensor of claim 1, wherein the flat detector strip comprises a first edge and a second edge between the first and second ends of the detector strip, the second edge being opposite the first edge across a width of the detector strip, at least one of the first edge or the second edge being linear between the first end and the second end of the detector strip.

13. The noninvasive L-shaped sensor of claim 12, wherein the first edge and the second edge are linear between the first end and the second end of the detector strip such that the detector strip is rectangular in shape.

14. The noninvasive L-shaped sensor of claim 12, wherein another one of the first edge or the second edge is non-linear and includes a transition portion.

15. The noninvasive L-shaped sensor of claim 14, wherein the transition portion is a sloped transition portion.

16. The noninvasive L-shaped sensor of claim 1, wherein the optical emitter comprises more than one LED.

* * * * *